United States Patent
Komada et al.

(10) Patent No.: US 7,595,277 B2
(45) Date of Patent: Sep. 29, 2009

(54) CATALYST FOR OXIDATION OR AMMOXIDATION

(75) Inventors: Satoru Komada, Yokosuka (JP); Sadao Shoji, Yokosuka (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 542 days.

(21) Appl. No.: 10/556,366

(22) PCT Filed: Jun. 9, 2003

(86) PCT No.: PCT/JP03/07274

§ 371 (c)(1), (2), (4) Date: Nov. 10, 2005

(87) PCT Pub. No.: WO2004/108278

PCT Pub. Date: Dec. 16, 2004

(65) Prior Publication Data

US 2006/0235238 A1    Oct. 19, 2006

(51) Int. Cl.
*B01J 23/00*    (2006.01)

(52) U.S. Cl. ............ 502/312; 558/323; 562/535

(58) Field of Classification Search ............ 502/312
See application file for complete search history.

(56) References Cited

U.S. PATENT DOCUMENTS

| | | | | |
|---|---|---|---|---|
| 4,008,179 | A | * | 2/1977 | Gasson et al. ........... 502/209 |
| 4,784,979 | A | | 11/1988 | Toft et al. |
| 5,750,760 | A | * | 5/1998 | Ushikubo et al. ........ 558/319 |
| 5,994,580 | A | | 11/1999 | Takahashi et al. |
| 6,036,880 | A | * | 3/2000 | Komada et al. ........ 252/183.13 |
| 6,514,902 | B1 | | 2/2003 | Inoue et al. |
| 6,610,629 | B2 | * | 8/2003 | Hinago et al. ........... 502/300 |
| 7,109,144 | B2 | | 9/2006 | Hinago et al. |
| 2002/0183548 | A1 | | 12/2002 | Bogan, Jr. et al. |

FOREIGN PATENT DOCUMENTS

| | | |
|---|---|---|
| CN | 1360971 A | 7/2002 |
| EP | 0 294 845 | 12/1988 |
| EP | 0 320 124 A1 | 6/1989 |
| EP | 0 529 853 | 3/1993 |
| EP | 0 895 809 A1 | 2/1999 |
| EP | 0 767 164 B1 | 8/1999 |
| EP | 1 146 067 A1 | 10/2001 |
| EP | 1 254 708 A2 | 11/2002 |
| JP | 10-28862 | 2/1998 |
| JP | 10-45664 | 2/1998 |
| JP | 11-169716 | 6/1999 |
| JP | 11-285646 | 10/1999 |
| JP | 2001-58827 | 3/2001 |
| JP | 2001-213855 | 8/2001 |
| JP | 2002-301373 | 10/2002 |
| JP | 2002-316052 | 10/2002 |
| JP | 2003-71284 | 3/2003 |

OTHER PUBLICATIONS

European Search Report for Application No. 03736099.7 dated Jan. 8, 2009.
Novakova, Ekaterina K. et al., "Propane Oxidation on No-V-Sb-Nb Mixed Oxide Catalysts," Journal of Catalysts 211, 235-243 (2002).
First Office Action for Chinese Patent Application No. 200380110318.5.
Second Office Action for Chinese Patent Application No. 200380110318.5.

* cited by examiner

*Primary Examiner*—Melvin C Mayes
*Assistant Examiner*—Melissa Stalder
(74) *Attorney, Agent, or Firm*—Finnegan, Henderson, Farabow, Garrett & Dunner, L.L.P.

(57) ABSTRACT

Disclosed is a catalyst for use in catalytic oxidation or ammoxidation of propane or isobutane in the gaseous phase, which comprises an oxide containing, in specific atomic ratios, molybdenum (Mo), vanadium (V), niobium (Nb) and antimony (Sb), wherein the oxide catalyst has a reduction ratio of from 8 to 12% and a specific surface area of from 5 to 30 $m^2/g$. Also disclosed is a process for efficiently producing this catalyst.

20 Claims, No Drawings

CATALYST FOR OXIDATION OR AMMOXIDATION

BACKGROUND OF THE INVENTION

1. Field of the Invention

The present invention relates to a catalyst for use in catalytic oxidation or ammoxidation of propane or isobutane in the gaseous phase. More particularly, the present invention is concerned with an oxide catalyst for oxidation or ammoxidation, which comprises an oxide containing, in specific atomic ratios, molybdenum (Mo), vanadium (V), niobium (Nb) and antimony (Sb), wherein the oxide catalyst has a reduction ratio of from 8 to 12% and a specific surface area of from 5 to 30 $m^2/g$. The present invention is also concerned with a process for efficiently producing this catalyst. The catalyst of the present invention is advantageous not only in that the selectivity for and yield of the desired product in the oxidation or ammoxidation are high, but also in that the catalyst exhibits only a small lowering of the yield of the desired product even in a long reaction time. Therefore, when the catalyst of the present invention is used for performing a catalytic oxidation or ammoxidation of propane or isobutane in the gaseous phase, an unsaturated carboxylic acid or an unsaturated nitrile (namely, (meth)acrylic acid or (meth)acrylonitrile) can be produced stably in high yield for a long period of time. Further, since the catalyst of the present invention exhibits only a small lowering of the yield with the passage of reaction time, the catalyst of the present invention is also advantageous in that, when a molybdenum compound is added to the catalytic oxidation or ammoxidation reaction system as conventionally practiced in the art for the purpose of maintaining a high yield by preventing a catalyst degradation caused by the volatilization or escaping of molybdenum from the catalyst, the amount of molybdenum compound added and the frequency of addition of molybdenum compound can be decreased, as compared to the case of the use of conventional catalysts, so that the reaction can be performed economically. In addition, the catalyst of the present invention is advantageous in that a moderate catalyst activity can be exhibited, and hence there can be prevented problems that too large an amount of catalyst is required for the reaction, thus causing too heavy a load on the reactor and that the heat of reaction generated becomes too large, rendering it impossible to effect a satisfactory heat removal from the reaction system.

2. Prior Art

Conventionally, there have been well known a process for producing (meth)acrylonitrile by ammoxidation of propylene or isobutylene, and a process for producing (meth)acrylic acid by oxidation of propylene or isobutylene. Recently, as substitutes for such processes for the oxidation and ammoxidation of propylene or isobutylene, attention has been attracted to a process for producing (meth)acrylonitrile by a catalytic ammoxidation of propane or isobutane in the gaseous phase, and a process for producing (meth)acrylic acid by a catalytic oxidation of propane or isobutane.

As catalysts which can be used for increasing the selectivity and yield in the reactions used in these processes, a number of oxide catalysts containing molybdenum, vanadium, niobium and antimony have been proposed.

For example, various catalyst compositions intended for producing (meth)acrylonitrile or (meth)acrylic acid with high selectivity and in high yield are disclosed in various patent documents, such as Unexamined Japanese Patent Application Laid-Open Specification Nos. Hei 9-157241 (corresponding to U.S. Pat. No. 5,750,760 and EP 767164B1), Hei 10-45664, and 2002-239382 (corresponding to U.S. Pat. No. 7,109,144 B2, US 2002/0115879 A1 and US 2006/0252954 A1).

Further, there are prior art documents which disclose the average valence of the component elements of a catalyst or disclose the atomic ratio of oxygen in a catalyst formulation. For example, Unexamined Japanese Patent Application Laid-Open Specification No. 2002-301373 has a description about the average valence of the component elements (other than the carrier) of a catalyst. Specifically, this patent document states that the average valence is generally from 4 to less than 6, preferably from 4.5 to 5.9, more preferably from 5 to 5.8. Unexamined Japanese Patent Application Laid-Open Specification No. 2003-24790 (corresponding to U.S. Patent Application Publication No. US 2002/0183548 A1 and EP 1254708A2) states that the representative atomic ratio of oxygen in a catalyst formulation is from 3 to 4.7, relative to molybdenum.

However, the catalysts (containing molybdenum, vanadium, niobium and antimony) disclosed in these patent documents are still unsatisfactory with respect to performance and hence cannot be commercially advantageously employed.

There are known various methods for producing catalysts which can increase the selectivity for and yield of the desired product in oxidation or ammoxidation. For example, such methods for producing catalysts are disclosed in Unexamined Japanese Patent Application Laid-Open Specification No. Hei 10-28862, EP 895809A1, Unexamined Japanese Patent Application Laid-Open Specification Nos. 2001-58827, 2002-301373, 2002-316052 and 2003-24790 (corresponding to U.S. Patent Application Publication No. US 2002/0183548 A1 and EP 1254708A2).

Especially, there are prior art documents which provide a teaching about a calcination method used in a method for producing a catalyst which can increase the selectivity for and yield of the desired product in oxidation or ammoxidation. For example, Unexamined Japanese Patent Application Laid-Open Specification No. Hei 9-157241 (corresponding to U.S. Pat. No. 5,750,760 and EP 767164B1) states that the calcination may be performed in an oxygen-containing atmosphere, but is preferably performed in an oxygen-free atmosphere. Unexamined Japanese Patent Application Laid-Open Specification No. Hei 10-28862 states that the calcination may be conducted using either a fluidized-bed kiln or a rotary kiln or using these kilns in combination. Unexamined Japanese Patent Application Laid-Open Specification No. Hei 10-45664 states that, prior to conducting the calcination, the catalyst precursor may be subjected to a thermal decomposition in the air to remove the most of volatile components from the catalyst precursor. Further, Unexamined Japanese Patent Application Laid-Open Specification No. 2002-316052 states that, in the case of a continuous calcination, the calcination is performed while supplying an inert gas at a flow rate of from 500 to 10,000 N liters per 1 kg of the supplied catalyst precursor, thereby effecting a thermal decomposition of the catalyst precursor.

However, with respect to the calcination methods employed in these prior art documents, there has not yet been found an important factor greatly influencing the selectivity for and yield of the desired product which are exhibited by the obtained catalyst. Therefore, the selectivity for and yield of the desired product which are exhibited by the catalysts produced by employing the conventional methods are not satisfactory from the commercial viewpoint.

A catalyst for commercial use not only needs to exhibit a high yield at the early stage of the reaction, but also needs to maintain the yield even when the reaction is performed for a long time (specifically, 1,500 hours or more). When the yield cannot be maintained for a long reaction time, it is conceivable to take the deactivated catalyst out of the reactor and feed a fresh catalyst into the reactor; however, such replacement of the deactivated catalyst by a fresh catalyst has a problem in that the replacement operation is cumbersome, hinders the continuous operation of the reactor and is also disadvantageous from the economic viewpoint. It is also conceivable to take a measure in which the degraded catalyst is taken out of the reactor and subjected to a regeneration operation to thereby obtain a regenerated catalyst, which is then returned to the reactor; however, this measure poses a problem in that the regeneration operation takes a long time and needs a complicated regeneration equipment and/or that a satisfactory regeneration of the catalyst cannot be achieved. Accordingly, there has been a demand for an excellent catalyst which exhibits only a small lowering of the yield of the desired product in a catalytic oxidation or ammoxidation reaction. For example, Unexamined Japanese Patent Application Laid-Open Specification No. 2002-239382 (corresponding to U.S. Pat. No. 7,109,144 B2, US 2002/0115879 A1 and US 2006/0252954 A1) discloses a catalyst which maintains the selectivity at almost the same level, although the selectivity can be maintained only for a relatively short reaction time of about 1,000 hours. However, this catalyst exhibits a low activity and hence a low conversion of propane fed; therefore, when this catalyst is used in a one pass mode of reaction, the yield of the desired product is not high. When a catalyst exhibits a low conversion of propane, it is conceivable to take a measure in which the unreacted propane is separated and recovered from the gas flowing out of the reactor and recycled to the reactor; however, this measure is disadvantageous in that the process of separation, recovery and recycling of the unreacted propane requires a large scale equipment. Unexamined Japanese Patent Application Laid-Open Specification No. Hei 11-169716 discloses a catalyst which maintains the yield at almost the same level, although the yield can be maintained only for a relatively short reaction time of about 1,300 hours. However, the working examples of this patent document employ a catalyst which contains tellurium but no antimony, and there is no specific description of a catalyst containing molybdenum, vanadium, niobium and antimony. Further, when a catalyst containing tellurium is used in a commercial scale reaction, a problem tends to arise in that the tellurium volatilizes and escapes from the catalyst with the passage of reaction time, thus destabilizing the reaction and rendering it difficult to commercially perform the reaction for a long time. In Unexamined Japanese Patent Application Laid-Open Specification No. Hei 2-2877 (corresponding to U.S. Patent No. 4,784,979 and EP 320124A), there is a description of a redox reaction of antimony and vanadium, but there is no technical concept of controlling the reduction ratio of a catalyst. In addition, it is presumed that the reduction ratio of a catalyst which is produced under the catalyst production conditions used in the working examples of this patent document would be much lower than 8%.

On the other hand, with respect to a catalyst containing molybdenum, there are cases where the catalyst is degraded by the volatilization and escaping of molybdenum from the catalyst, although the degree of the degradation is small, as compared to the degradation caused by the volatilization and escaping of tellurium. For preventing this degradation, there has conventionally been known a method in which a molybdenum compound is added to the reactor during the reaction.

For example, Unexamined Japanese Patent Application Laid-Open Specification No. 2001-213855 discloses a process for producing an unsaturated nitrile stably in a high yield by using a catalyst containing molybdenum, vanadium, niobium and antimony, wherein the process involves a step of adding to the reaction system a compensative compound comprising at least one compound selected from the group consisting of a tellurium compound and a molybdenum compound. In this patent document, the amount of the compensative compound is described to be such that the weight ratio of the compensative compound to the catalyst is equal to or less than 0.1/1, preferably equal to or less than 0.02/1. In Example 2 of this patent document, it is described that a reaction is performed for 53 hours in total, wherein during the reaction, both a tellurium compound and a molybdenum compound are simultaneously added to the reaction system, each in an amount of 0.1 g, relative to 45 g of the catalyst (namely, the weight ratio of each compound to the catalyst is 0.0022/1). This means that the amount of molybdenum compound which added to the reaction system per hour of the reaction time is such that the weight ratio of the molybdenum compound to the catalyst is as large as 0.000042/1; that is, a large amount of molybdenum compound is added to the reaction system. In the case where a molybdenum compound is added to a reaction system for the purpose of maintaining the yield, when the molybdenum compound is added in a large amount, there occur problems not only in that the cost of the molybdenum compound becomes large, which is economically disadvantageous, but also in that, when the reaction is conducted using a fluidized-bed reactor, the molybdenum compound added adheres to the heat removal coil in the reactor, thus hindering the transfer of heat to the heat removal coil and rendering it impossible to perform a stable reaction. Therefore, there has been a demand for a catalyst which has an advantage in that, in performing the conventional practice of adding a molybdenum compound to the reaction system, the amount of molybdenum compound added and the frequency of addition of molybdenum compound can be decreased to a level as low as possible.

For producing a desired product stably and economically on a commercial scale, it is especially important to maintain the yield of the desired product at a high level for more than 1,500 hours from the start of the reaction. In this respect, there has been a demand for a catalyst which can exhibit a performance such that, even more than 1,500 hours after the start of the reaction, a high yield can be maintained by the addition of only a small amount of molybdenum compound to the reaction system. However, there has not yet been known an excellent catalyst which exhibits only a small lowering of the yield of the desired product, thereby enabling the maintenance of a high yield by the addition of only a small amount of molybdenum compound during the reaction.

Further, it should be noted that, with respect to a catalyst which is commercially used in a catalytic oxidation or ammoxidation of propane or isobutane in the gaseous phase, the catalyst is required to exhibit an important performance such that, in addition to high yield and high stability of the yield with the passage of reaction time, the catalyst exhibits a moderate activity. In general, when a catalyst having low activity is used in a catalytic oxidation or ammoxidation, the catalyst is used in an increased amount for the purpose of obtaining a desired conversion of a raw material used. In such a case, however, when the activity of the catalyst is too low, disadvantages occur not only in that too large an amount of catalyst is necessary, but also in that the load on the reactor becomes large, and the size of the reactor needs to be increased.

In the case of a catalyst having too low an activity, it is naturally conceivable to take a measure in which the catalytic activity is increased by raising the reaction temperature; however, this measure poses a problem not only in that, when the reaction temperature is raised to a level which is higher than an appropriate temperature, the yield of the desired product is decreased, but also in that, in the case of an ammoxidation reaction, the ammonium used as a raw material is wastefully burnt without being used for producing the desired product. Also, the use of too high a reaction temperature is undesired because of the occurrence of adverse effects on the material of the reactor.

On the other hand, when a catalyst having too high an activity is used in a catalytic oxidation or ammoxidation, there is a problem in that the conversion of a raw material used is increased too much, leading to a lowering of the yield of the desired product and a generation of too great an amount of heat of reaction. Therefore, it is conceivable to take a measure in which the amount of catalyst used is decreased. However, this measure poses the following problem. With respect to a fluidized-bed reactor which is used for performing a catalytic oxidation or ammoxidation on a commercial scale, the fluidized-bed reactor is equipped with a heat removal coil designed for removing the heat of reaction generated during the oxidation or ammoxidation. In this case, when the amount of the catalyst used is decreased in an attempt to prevent the adverse effects of too high a catalytic activity, the decrease in the amount of the catalyst results in a decrease in the contact area between the catalyst and the heat removal coil, thus rendering it impossible to effect a satisfactory heat removal and continue the operation of the reactor. There is a further problem in that the amount of the raw material gas per unit weight of the catalyst becomes too large, which tends to cause a degradation of the catalyst. It is conceivable to take a measure in which the catalytic activity is decreased by lowering the reaction temperature; however, this measure poses a problem in that the selectivity for the desired product is decreased.

As seen from the above, there has not yet been known a catalyst which is advantageous not only in that the selectivity for and yield of the desired product in the oxidation or ammoxidation are high, but also in that the catalyst exhibits only a small lowering of the yield of the desired product even in a long reaction time, and the yield of the desired product can be easily maintained at a high level for a long reaction time, while exhibiting a moderate catalyst activity.

SUMMARY OF THE INVENTION

In this situation, the present inventors have made extensive and intensive studies with a view toward solving above-mentioned problems of the prior art, specifically toward developing an excellent oxide catalyst containing molybdenum, vanadium, niobium and antimony, which is for use in a catalytic oxidation or ammoxidation of propane or isobutane in the gaseous phase, and toward developing a process for producing such excellent catalyst. As a result, it has unexpectedly been found that this objective can be attained by a catalyst which comprises an oxide containing, in specific atomic ratios, molybdenum (Mo), vanadium (V), niobium (Nb) and antimony (Sb), wherein the oxide catalyst has a reduction ratio of from 8 to 12% and a specific surface area of from 5 to 30 m²/g. That is, it has unexpectedly been found that such catalyst exhibits excellent properties: that a moderate catalyst activity can be exhibited; that the results of the reaction (selectivity for and yield of the desired product) are satisfactory; and that the catalyst exhibits only a small lowering of the yield of the desired product even in a long reaction time, and therefore a lowering of the yield can be easily prevented by the addition of only a small amount of molybdenum compound and with less frequency of the addition even in a long reaction time. The present inventors have also found that this catalyst can be efficiently produced by a catalyst production process employing specific conditions for calcination. Based on these findings, the present invention has been completed.

Accordingly, it is an object of the present invention to provide a catalyst for use in catalytic oxidation or ammoxidation of propane or isobutane in the gaseous phase, which comprises an oxide containing, in specific atomic ratios, molybdenum (Mo), vanadium (V), niobium (Nb) and antimony (Sb), wherein the catalyst is advantageous not only in that the catalyst exhibits a high yield of the desired product and is capable of maintaining the yield at a high level for a long reaction time by adding to the reaction system only a small amount of molybdenum compound and with less frequency of the addition, but also in that a moderate catalyst activity can be exhibited.

It is another object of the present invention to provide a process for efficiently producing the above-mentioned catalyst.

It is still another object of the present invention to provide a process for producing an unsaturated carboxylic acid or an unsaturated nitrile (namely, (meth)acrylic acid or (meth)acrylonitrile) by using the above-mentioned catalyst.

DETAILED DESCRIPTION OF THE INVENTION

In one aspect of the present invention, there is provided a catalyst for use in catalytic oxidation or ammoxidation of propane or isobutane in the gaseous phase, which comprises an oxide represented by the following formula (1):

$$Mo_1V_aNb_bSb_cO_n \quad (1)$$

wherein:
a, b, c and n are, respectively, the atomic ratios of vanadium (V), niobium (Nb), antimony (Sb) and oxygen (O), relative to molybdenum (Mo),
wherein:

$0.1 \leq a \leq 1$, $0.01 \leq b \leq 1$, $0.01 \leq c \leq 1$, and n is the number of oxygen atoms required to satisfy the valence requirements of the other component elements present, the catalyst having a reduction ratio of from 8 to 12% and a specific surface area of from 5 to 30 m²/g,
the reduction ratio being represented by the following formula (2):

$$\text{reduction ratio (\%)} = ((n_0-n)/n_0) \times 100 \quad (2)$$

wherein:
n is as defined for formula (1), and
$n_0$ is the number of oxygen atoms required when the other component elements in the oxide of formula (1) respectively exhibit the maximum oxidation numbers of the other component elements.

In another aspect of the present invention, there is provided a process for producing the above-mentioned catalyst, which comprises the steps of:

providing an aqueous raw material mixture containing compounds of molybdenum, vanadium, niobium and antimony, drying the aqueous raw material mixture to thereby obtain a dried catalyst precursor, and calcining the dried catalyst precursor under calcination conditions wherein the heating temperature of the dried catalyst precursor is continuously or intermittently elevated from a temperature which is less than 400° C. to a temperature which is in the range of from 550 to 700° C., wherein the calcination conditions are adjusted so that the catalyst precursor being calcined has a reduction ratio of from 8 to 12% when the heating temperature reaches 400° C., wherein the reduction ratio is as defined above in connection with the above-mentioned catalyst, thereby obtaining a catalyst having a reduction ratio of from 8 to 12% and a specific surface area of from 5 to 30 m²/g.

For easy understanding of the present invention, the essential features and various preferred embodiments of the present invention are enumerated below.

1. A catalyst for use in catalytic oxidation or ammoxidation of propane or isobutane in the gaseous phase, which comprises an oxide represented by the following formula (1):

$$Mo_1V_aNb_bSb_cO_n \quad (1)$$

wherein:

a, b, c and n are, respectively, the atomic ratios of vanadium (V), niobium (Nb), antimony (Sb) and oxygen (O), relative to molybdenum (Mo), wherein:

$0.1 \leq a \leq 1$, $0.01 \leq b \leq 1$, $0.01 \leq c \leq 1$, and n is the number of oxygen atoms required to satisfy the valence requirements of the other component elements present, the catalyst having a reduction ratio of from 8 to 12% and a specific surface area of from 5 to 30 m²/g, the reduction ratio being represented by the following formula (2):

$$\text{reduction ratio } (\%) = ((n_0 - n)/n_0) \times 100 \quad (2)$$

wherein:

n is as defined for formula (1), and $n_0$ is the number of oxygen atoms required when the other component elements in the oxide of formula (1) respectively exhibit the maximum oxidation numbers of the other component elements.

2. The catalyst according to item 1 above, wherein a, b and c in formula (1) are as follows:

$0.1 \leq a \leq 0.3$, $0.05 \leq b \leq 0.2$, $0.1 \leq c \leq 0.3$.

3. The catalyst according to item 1 or 2 above, which further comprises a silica carrier having supported thereon the oxide, wherein the silica carrier is present in an amount of from 20 to 60% by weight in terms of $SiO_2$, based on the total weight of the oxide and the silica carrier.

4. The catalyst according to any one of items 1 to 3 above, wherein no in formula (2) is from 4 to 5.

5. A process for producing the catalyst of item 1 above, which comprises the steps of:

providing an aqueous raw material mixture containing compounds of molybdenum, vanadium, niobium and antimony, drying the aqueous raw material mixture to thereby obtain a dried catalyst precursor, and calcining the dried catalyst precursor under calcination conditions wherein the heating temperature of the dried catalyst precursor is continuously or intermittently elevated from a temperature which is less than 400° C. to a temperature which is in the range of from 550 to 700° C., wherein the calcination conditions are adjusted so that the catalyst precursor being calcined has a reduction ratio of from 8 to 12% when the heating temperature reaches 400° C., wherein the reduction ratio is as defined in item 1 above, thereby obtaining a catalyst having a reduction ratio of from 8 to 12% and a specific surface area of from 5 to 30 m²/g.

6. The process according to item 5 above, wherein the aqueous raw material mixture is obtained by mixing an aqueous mixture (A) containing compounds of molybdenum, vanadium and antimony with an aqueous liquid (B) containing a niobium compound.

7. The process according to item 6 above, wherein the aqueous mixture (A) is obtained by heating, at 50° C. or more, compounds of molybdenum, vanadium and antimony in an aqueous solvent.

8. The process according to item 7 above, wherein, after the heating, hydrogen peroxide is added to the aqueous mixture (A).

9. The process according to item 8 above, wherein the amount of the hydrogen peroxide is such that the molar ratio ($H_2O_2$/Sb molar ratio) of the hydrogen peroxide to the antimony compound in terms of antimony is in the range of from 0.01 to 20.

10. The process according to item 6 above, wherein the aqueous liquid (B) contains a dicarboxylic acid in addition to the niobium compound, wherein the molar ratio (dicarboxylic acid/Nb molar ratio) of the dicarboxylic acid to the niobium compound in terms of niobium is in the range of from 1 to 4.

11. The process according to item 6 or 10 above, wherein at least a part of the aqueous liquid (B) containing a niobium compound is used in the form of a mixture thereof with hydrogen peroxide.

12. The process according to item 11 above, wherein the amount of the hydrogen peroxide is such that the molar ratio ($H_2O_2$/Nb molar ratio) of the hydrogen peroxide to the niobium compound in terms of niobium is in the range of from 0.5 to 20.

13. The process according to item 6 or 10 above, wherein at least a part of the aqueous liquid (B) containing a niobium compound is used in the form of a mixture thereof with hydrogen peroxide and an antimony compound.

14. The process according to item 13 above, wherein:

the amount of the hydrogen peroxide is such that the molar ratio ($H_2O_2$/Nb molar ratio) of the hydrogen peroxide to the niobium compound in terms of niobium is in the range of from 0.5 to 20, and the amount of the antimony compound mixed with the at least a part of the aqueous liquid (B) and the hydrogen peroxide is such that the molar ratio (Sb/Nb molar ratio) of the antimony compound in terms of antimony to the niobium compound in terms of niobium is not more than 5.

15. The process according to item 5 above, wherein at least a part of the calcination is performed in an atmosphere of an inert gas, wherein:

when the calcination is performed in a batchwise manner, the inert gas is supplied at a flow rate of not less than 50 N liters/hour/kg of the dried catalyst precursor, and when the calcination is performed in a continuous manner, the inert gas is supplied at a flow rate of not less than 50 N liters/kg of the dried catalyst precursor.

16. The process according to item 5 or 15 above, wherein the calcination comprises a preliminary calcination and a final calcination, wherein the preliminary calcination is performed at a temperature in the range of from 250 to 400° C.

and the final calcination is performed at a temperature in the range of from 550 to 700° C.

17. The process according to item 5, 15 or 16 above, wherein, during the calcination, an oxidant or a reductant is added to an atmosphere in which the calcination is performed, so as to cause the catalyst precursor being calcined to have a reduction ratio of from 8 to 12% when the heating temperature reaches 400° C.
18. The process according to item 17 above, wherein the oxidant is oxygen gas.
19. The process according to item 17 above, wherein the reductant is ammonia.
20. A process for producing acrylic acid or methacrylic acid, which comprises reacting propane or isobutane with molecular oxygen in the gaseous phase in the presence of the catalyst of item 1 above.
21. A process for producing acrylonitrile or methacrylonitrile, which comprises reacting propane or isobutane with ammonia and molecular oxygen in the gaseous phase in the presence of the catalyst of item 1 above.

Hereinbelow, the present invention is described in detail.

The catalyst of the present invention comprises molybdenum, vanadium, niobium and antimony as the component elements thereof.

The catalyst of the present invention comprises an oxide represented by the following formula (1):

$$Mo_1V_aNb_bSb_cO_n \quad (1)$$

wherein:
a, b, c and n are, respectively, the atomic ratios of vanadium (V), niobium (Nb), antimony (Sb) and oxygen (O), relative to molybdenum (Mo),
wherein:

$$0.1 \leq a \leq 1,$$

$$0.01 \leq b \leq 1,$$

$$0.01 \leq c \leq 1, \text{ and}$$

n is the number of oxygen atoms required to satisfy the valence requirements of the other component elements present.

In the above-mentioned formula (1), it is preferred that a, b and c (respectively representing the atomic ratios of vanadium (V), niobium (Nb) and antimony (Sb), relative to molybdenum (Mo)) are as follows: $0.1 \leq a \leq 0.5$, $0.01 \leq b \leq 0.5$, $0.01 \leq c \leq 0.5$, more advantageously $0.1 \leq a \leq 0.3$, $0.05 \leq b \leq 0.2$, $0.1 \leq c \leq 0.3$.

When the reaction mode is a fluidized-bed reaction, the catalyst is required to have high strength. Therefore, in such a case, it is preferred that the catalyst of the present invention is used in a form such that the oxide of formula (1) is supported on a sufficient amount of a silica carrier for providing satisfactory strength.

When the catalyst of the present invention further comprises a silica carrier, it is preferred that the silica carrier has supported thereon the oxide, wherein the silica carrier is present in an amount of from 20 to 60% by weight, more advantageously from 30 to 50% by weight, in terms of $SiO_2$, based on the total weight of the oxide and the silica carrier.

When the amount of the silica carrier in the catalyst is smaller than 20% by weight, the strength of the catalyst becomes unsatisfactory, so that the catalyst is likely to become powdery during the reaction and escape from the reactor, thus posing problems in that it becomes impossible to perform a stable reaction on a commercial scale and that economic disadvantages are caused as it is required to supply an additional amount of the catalyst to compensate for the catalyst loss.

On the other hand, when the amount of the silica carrier in the catalyst is larger than 60% by weight, there cannot be obtained a satisfactory activity, and hence the amount of catalyst necessary for the reaction is increased. Especially, in the case where the reaction mode is a fluidized-bed reaction, when the amount of the silica carrier in the catalyst is larger than 60% by weight, the specific gravity of the catalyst becomes too small, rendering it difficult to achieve an excellent flow.

The catalyst of the present invention has a reduction ratio of from 8 to 12%, preferably from 9 to 11%. When the reduction ratio is lower than 8%, the selectivity for the desired product becomes low, and further, the activity of the catalyst becomes extremely low. On the other hand, when the reduction ratio is higher than 12%, the activity of the catalyst becomes low, and further, the selectivity for the desired product becomes extremely low.

In the present invention, the reduction ratio is represented by the following formula (2):

$$\text{reduction ratio } (\%) = ((n_0 - n)/n_0) \times 100 \quad (2)$$

wherein:
n is as defined for formula (1), and
$n_0$ is the number of oxygen atoms required when the other component elements in the oxide of formula (1) respectively exhibit the maximum oxidation numbers of the other component elements.

$n_0$ in formula (2) can be obtained by calculation from the ratios of the component elements contained in the raw materials employed. The maximum oxidation numbers of the component elements are as follows: molybdenum has a maximum oxidation number of 6; vanadium has a maximum oxidation number of 5, niobium has a maximum oxidation number of 5; and antimony has a maximum oxidation number of 5. When the catalyst contains a component element (e.g., tungsten) other than molybdenum, vanadium, niobium, antimony and oxygen, n and $n_0$ are determined so that the valence of the other component element and the atomic ratio of the other component element, relative to molybdenum, are reflected.

It is preferred that $n_0$ in formula (2) is from 4 to 5.

In the present invention, the specific surface area of the catalyst is measured by the BET method, namely the method based on the BET adsorption isotherm (i.e., the Brunauer-Emmett-Teller adsorption isotherm). The specific surface area of the catalyst of the present invention is from 5 to 30 $m^2/g$, preferably from 7 to 20 $m^2/g$.

When the specific surface area of the catalyst is smaller than 5 $m^2/g$, there cannot be obtained a satisfactory activity of the catalyst nor a high yield of the desired product. On the other hand, when the specific surface area of the catalyst is larger than 30 $m^2/g$, it is not sure that any increase in the activity can be obtained, and rather it is probable that the yield becomes poor and the activity is drastically degraded. Further, a problem arises in that, in the case of an ammoxidation reaction, the ammonium used as a raw material is wastefully burnt without being used for producing the desired product.

With respect to the effect of the addition of a molybdenum compound during a catalytic oxidation or ammoxidation reaction for the purpose of maintaining the yield of the desired product, the present inventors have unexpectedly found that the specific surface area of the catalyst used has a large influence on the effect of the addition. When the specific surface area of the catalyst is smaller than 5 m²/g, almost no effect can be achieved by the addition of a molybdenum compound. When the specific surface area of the catalyst is larger than 30 m²/g, the effect of the addition of a molybdenum compound can be exhibited for a while, but the effect will be lost in a short time, that is, shortly there occurs a degradation of the catalyst, thus making it necessary to increase the amount of the molybdenum compound added and increase the frequency of addition of the molybdenum compound. The reason why the specific surface area of the catalyst has such influence on the effect of the addition of a molybdenum compound has not yet been elucidated. However, it is presumed that, when the specific surface area of the catalyst is smaller than 5 m²/g, the effective surface area of the catalyst active species becomes too small, thus preventing the catalyst active species from fully receiving the effect of the addition of a molybdenum compound. It is also presumed that, when the specific surface area of the catalyst is larger than 30 m²/g, because the effective surface area of the catalyst active species is larger than 30 m²/g, the escaping of molybdenum from the catalyst active species is greatly accelerated disadvantageously.

In the present invention, the activity of the catalyst can be represented by the activity as measured at a reaction temperature of 440° C. Commercially, it is preferred that the activity is from 1.5 to 10($\times 10^3$ hour$^{-1}$), more advantageously from 2 to 6($\times 10^3$ hour$^{-1}$), still more advantageously from 2 to 4($\times 10^3$ hour$^{-1}$). In the present invention, the activity of the catalyst is defined by the following formula:

activity (hour$^{-1}$)=−3,600/(contact time)×ln((100−conversion of propane or isobutane)/100)

(wherein ln is natural logarithm)

Hereinbelow, explanations are made in detail on the process for producing the catalyst of the present invention.

The catalyst of the present invention can be efficiently produced by, for example, a process for producing the catalyst of the present invention, which comprises the steps of:

providing an aqueous raw material mixture containing compounds of molybdenum, vanadium, niobium and antimony, drying the aqueous raw material mixture to thereby obtain a dried catalyst precursor, and calcining the dried catalyst precursor under calcination conditions wherein the heating temperature of the dried catalyst precursor is continuously or intermittently elevated from a temperature which is less than 400° C. to a temperature which is in the range of from 550 to 700° C., wherein the calcination conditions are adjusted so that the catalyst precursor being calcined has a reduction ratio of from 8 to 12% when the heating temperature reaches 400° C., wherein the reduction ratio is as defined in connection with the catalyst of the present invention, thereby obtaining a catalyst having a reduction ratio of from 8 to 12% and a specific surface area of from 5 to 30 m²/g.

This process for producing the catalyst of the present invention is described in detail. This process for producing the catalyst of the present invention comprises the following steps: a step for providing an aqueous raw material mixture, a step for drying the aqueous raw material mixture to thereby obtain a dried catalyst precursor, and a step for calcining the dried catalyst precursor. These steps are described hereinbelow in detail.

<Aqueous Raw Material Mixture Preparation Step>

With respect to the molybdenum compound used as a source of molybdenum in the aqueous raw material mixture preparation step in the process of the present invention, there is no particular limitation. Preferred examples of molybdenum compounds include ammonium heptamolybdate and the like.

With respect to the vanadium compound as a source of vanadium, ammonium metavanadate and the like can be advantageously used.

With respect to the niobium compound as a source of niobium, there can be used at least one compound selected from the group consisting of niobic acid, an inorganic acid salt of niobium, an organic acid salt of niobium and the like. Of these, niobic acid is preferred.

Niobic acid is represented by the following formula: $Nb_2O_5 \cdot nH_2O$, which is also known as "niobium hydroxide or "niobium oxide hydrate".

As described in Unexamined Japanese Patent Application Laid-Open Specification No. Hei 11-47598, with respect to niobic acid, it is preferred to use niobic acid in the form of a niobic acid-containing aqueous mixture which contains niobic acid, a dicarboxylic acid (e.g. oxalic acid) and ammonia, wherein the molar ratio (dicarboxylic acid/Nb molar ratio) of the dicarboxylic acid to the niobic acid in terms of niobium is in the range of from 1 to 4 and the molar ratio (ammonia/Nb molar ratio) of the ammonia to the niobic acid in terms of niobium is 2 or less.

With respect to the antimony compound as a source of antimony, antimony oxide or the like can be advantageously used. Especially preferred is diantimony trioxide.

In the case of producing a silica carrier-supported catalyst of the present invention, a silica sol or a fumed silica can be advantageously used as a source of silica.

In the present invention, water is generally used as an aqueous medium, but in order to adjust the solubility of the compounds in the aqueous medium, if desired, there can be used water containing an alcohol in an amount within a range which does not cause any adverse effects on the catalyst obtained. Examples of alcohols used in the present invention include $C_1$-$C_4$ alcohols and the like.

Hereinbelow, a specific example of a method for preparing an aqueous raw material mixture is explained, taking as an example the case which uses the above-mentioned preferred raw material compounds as sources of the component elements of the oxide catalyst of the present invention.

Ammonium heptamolybdate, ammonium metavanadate and diantimony trioxide are added to water, followed by heating of the resultant mixture to thereby obtain an aqueous mixture (A). It is preferred that the heating is performed while stirring the mixture. It is preferred that the heating temperature is 50° C. or more, more advantageously in the range of from 50° C. to the boiling point, still more advantageously in the range of from 70° C. to the boiling point. It is further preferred that the heating temperature is in the range of from 80 to 100° C. The heating may be performed under reflux by using a reflux equipment having a condenser. Generally, in the case of heating under reflux, the boiling point is in the range of from about 101 to 102° C. The heating time is preferably 0.5 hour or more. When the heating temperature is low (e.g., lower than 50° C.), the heating time needs to be long. When the heating temperature is in the preferred range of from 80 to 100° C., the heating time is preferably in the range of from 1 to 5 hours.

It is preferred that, after the heating, hydrogen peroxide is added to the aqueous mixture (A). By employing this operation, the molybdenum and the vanadium which have been reduced during the preparation of the aqueous mixture (A) can be oxidized by the hydrogen peroxide added to the aqueous mixture (A). When hydrogen peroxide is added to the aqueous mixture (A), it is preferred that the amount of the hydrogen peroxide is such that the molar ratio ($H_2O_2$/Sb molar ratio) of the hydrogen peroxide to the antimony compound in terms of antimony is in the range of from 0.01 to 20, more advantageously in the range of from 0.5 to 3, still more advantageously in the range of from 1 to 2.5. It is preferred that, after the addition of hydrogen peroxide, the aqueous mixture (A) is stirred at a temperature in the range of from 30 to 70° C. for 30 minutes to 2 hours.

A niobium compound (e.g., niobic acid) is added to water, followed by heating of the resultant mixture to thereby obtain an aqueous liquid (B). It is preferred that the heating temperature is in the range of from 50 to 100° C., more advantageously in the range of from 70 to 99° C., still more advantageously in the range of from 80 to 98° C. It is preferred that the aqueous liquid (B) contains a dicarboxylic acid (e.g., oxalic acid) in addition to the niobium compound, wherein the molar ratio (dicarboxylic acid/Nb molar ratio) of the dicarboxylic acid to the niobium compound in terms of niobium is in the range of from 1 to 4, more advantageously in the range of from 2 to 4. That is, in this case, niobic acid and oxalic acid are added to water, followed by heating and stirring of the resultant mixture to thereby obtain an aqueous liquid (B).

As a specific example of a method for preparing the above-mentioned aqueous liquid (B), there can be mentioned a method comprising the following steps (1) to (3):

(1) mixing water, a dicarboxylic acid (e.g. oxalic acid) and a niobium compound (e.g. niobic acid) to thereby obtain a preliminary niobium-containing aqueous solution or a niobium-containing aqueous semisolution having suspended therein a part of the niobium compound;

(2) cooling the preliminary niobium-containing aqueous solution or niobium-containing aqueous semisolution to thereby precipitate a part of the dicarboxylic acid; and (3) removing the precipitated dicarboxylic acid from the preliminary niobium-containing aqueous solution, or removing the precipitated dicarboxylic acid and the suspended niobium compound from the niobium-containing aqueous semisolution, thereby obtaining a niobium-containing aqueous liquid (B).

The aqueous liquid (B) obtained in the above method usually has a dicarboxylic acid/Nb molar ratio within the range of from 2 to 4.

In step (1) of this method, it is especially preferred that oxalic acid is used as the dicarboxylic acid. With respect to the niobium compound used in step (1) of this method, there can be mentioned niobic acid and niobium hydrogenoxalate. These niobium compounds can be used in the form of a solid or in the form of a dispersion in an appropriate medium.

When niobium hydrogenoxalate is used as the niobium compound, the dicarboxylic acid may not be used. When niobic acid is used as the niobium compound, in order to remove acidic impurities with which the niobic acid may have been contaminated during the production thereof, the niobic acid may be washed with an aqueous ammonia solution and/or water prior to use.

It is preferred to use, as the niobium compound, a freshly prepared niobium compound. However, in the above-mentioned method, a niobium compound can be used which is slightly denatured (for example by dehydration) as a result of a long-term storage and the like.

In step (1) of this method, the dissolution of the niobium compound can be promoted by the addition of a small amount of an aqueous ammonia or by heating.

The concentration of the niobium compound (in terms of niobium) in the preliminary niobium-containing aqueous solution or aqueous semisolution is preferably selected within the range of from 0.2 to 0.8 mol/kg of the solution or semisolution. The dicarboxylic acid is preferably used in an amount such that the molar ratio of the dicarboxylic acid to the niobium compound in terms of niobium is approximately 3 to 6. When an excess amount of the dicarboxylic acid is used, a large amount of the niobium compound can be dissolved in the aqueous solution of dicarboxylic acid; however, a disadvantage is likely to arise in that the amount of the dicarboxylic acid which is caused to precipitate by cooling the obtained preliminary niobium-containing aqueous solution or semisolution becomes too large, thus decreasing the utilization of the dicarboxylic acid. On the other hand, when an unsatisfactory amount of the dicarboxylic acid is used, a disadvantage is likely to arise in that a large amount of the niobium compound remains undissolved and is suspended in the aqueous solution of the dicarboxylic acid to form a semisolution, wherein the suspended niobium compound is removed from the semisolution, thus decreasing the degree of utilization of the niobium compound.

The cooling operation in step (2) is not particularly limited. The cooling can be performed simply, for example, by means of ice.

The removal of the precipitated dicarboxylic acid (or precipitated dicarboxylic acid and the dispersed niobium compound) in step (3) can be easily performed by a conventional method, for example, by decantation or filtration.

When the dicarboxylic acid/Nb molar ratio of the obtained niobium-containing aqueous solution is outside the range of from 2 to 4, either the niobium compound or dicarboxylic acid may be added to the aqueous liquid (B) so that the dicarboxylic acid/Nb molar ratio of the solution falls within the above-mentioned range. However, in general, such an operation is unnecessary since an aqueous liquid (B) having the dicarboxylic acid/Nb molar ratio within the range of from 2 to 4 can be prepared by appropriately controlling the concentration of the niobium compound, the ratio of the dicarboxylic acid to the niobium compound and the cooling temperature of the above-mentioned preliminary niobium-containing aqueous solution or semisolution.

Thus, the aqueous liquid (B) can be prepared in the manner described above. However, the aqueous liquid (B) may also be prepared so as to contain further component(s).

Specifically, it is preferred that at least a part of the aqueous liquid (B) containing a niobium compound or containing a mixture of a niobium compound and a dicarboxylic acid is used in the form of a mixture thereof with hydrogen peroxide. In this case, it is more preferred that the amount of the hydrogen peroxide is such that the molar ratio ($H_2O_2$/Nb molar ratio) of the hydrogen peroxide to the niobium compound in terms of niobium is in the range of from 0.5 to 20, more advantageously in the range of from 1 to 20.

It is also preferred that at least a part of the aqueous liquid (B) containing a niobium compound or containing a mixture of a niobium compound and a dicarboxylic acid is used in the form of a mixture thereof with hydrogen peroxide and an antimony compound (e.g. diantimony trioxide). In this case, it is more preferred that the amount of the hydrogen peroxide is such that the molar ratio ($H_2O_2$/Nb molar ratio) of the hydrogen peroxide to the niobium compound in terms of niobium is in the range of from 0.5 to 20, more advantageously in the range of from 1 to 20; and that the amount of the antimony compound mixed with the at least a part of the aqueous liquid (B) and the hydrogen peroxide is such that the molar ratio (Sb/Nb molar ratio) of the antimony compound in terms of antimony to the niobium compound in terms of niobium is not more than 5, more advantageously in the range of from 0.01 to 2.

The aqueous mixture (A) and aqueous liquid (B) are mixed together in an appropriate ratio in accordance with the desired composition of the catalyst, to thereby obtain an aqueous raw material mixture. Generally, the aqueous raw material mixture is obtained in the form of a slurry. The content of the aqueous medium in the aqueous raw material mixture is generally in the range of from 50 to less than 100% by weight, preferably in the range of from 70 to 95% by weight, more preferably in the range of from 75 to 90% by weight.

In the case of producing a silica carrier-supported catalyst of the present invention, the aqueous raw material mixture is prepared so as to contain a source of silica (namely, a silica sol or a fumed silica). The amount of the source of silica can be appropriately adjusted in accordance with the amount of the silica carrier in the catalyst to be obtained.

<Drying Step>

The above-obtained aqueous raw material mixture is dried to thereby obtain a dried catalyst precursor. The drying can be conducted by conventional methods, such as spray drying or evaporation drying. It is preferred that a spray drying method is employed to thereby obtain a fine, spherical dried catalyst precursor. The spray drying can be conducted by centrifugation, by the two-phase flow nozzle method or by the high pressure nozzle method. As a heat source for drying, it is preferred to use air which has been heated by steam, an electric heater and the like. It is preferred that the temperature of the spray dryer at an entrance to the dryer section thereof is from 150 to 300° C., and that the temperature of the spray dryer at an exit from the dryer section thereof is from 100 to 160° C.

<Calcination Step>

In the calcination step, the dried catalyst precursor obtained in the drying step is calcined so as to obtain an oxide catalyst. The calcination can be conducted by using a rotary kiln, a fluidized-bed kiln or the like. When the calcination of the dried catalyst precursor is conducted in a stationary state, problems possibly arise in that the dried catalyst precursor cannot be evenly calcined, thus leading to a deterioration of the properties of the catalyst obtained and also to a breakage or cracking of the catalyst obtained.

The calcination is conducted so that the obtained oxide catalyst can have a reduction ratio of from 8 to 12% and a specific surface are of from 5 to 30 $m^2/g$. Specifically, the calcination is conducted under calcination conditions wherein the heating temperature of the dried catalyst precursor is continuously or intermittently elevated from a temperature which is less than 400° C. to a temperature which is in the range of from 550 to 700° C., wherein the calcination conditions are adjusted so that the catalyst precursor being calcined has a reduction ratio of from 8 to 12% when the heating temperature reaches 400° C., thereby obtaining a catalyst having a reduction ratio of from 8 to 12% and a specific surface area of from 5 to 30 $m^2/g$.

The calcination can be conducted in air or under a flow of air. However, at least a part of the calcination is preferably conducted in an atmosphere of an inert gas (e.g., under a flow of an inert gas), such as nitrogen gas which is substantially free of oxygen.

Especially, when the above-mentioned aqueous raw material mixture preparation step contains an operation in which hydrogen peroxide is added to the aqueous mixture (A), thereby oxidizing molybdenum and vanadium in the aqueous mixture (A) almost to their respective maximum oxidation numbers, it is preferred that the calcination of the obtained dried catalyst precursor is conducted under a flow of an inert gas, such as nitrogen gas which is substantially free of oxygen. The dried catalyst precursor generally contains an ammonium radical, an organic acid, an inorganic acid and the like, as well as some water. When the calcination is conducted under a flow of an inert gas which is substantially free of oxygen, those compounds contained in the dried catalyst precursor undergo evaporation, decomposition and the like, wherein these evaporation, decomposition and the like cause a reduction of the component elements in the catalyst precursor. When the component elements in the dried catalyst precursor to be subjected to the calcination respectively exhibit almost the maximum oxidation numbers thereof, the desired range of reduction ratio of the catalyst can be achieved simply by conducting the calcination so as to cause the component elements to undergo a reduction during the calcination; thus, in this case, the calcination can be conducted in a simple, commercially advantageous manner.

On the other hand, it is also possible to add an oxidant or a reductant to the atmosphere in which the calcination is performed, to thereby obtain the desired range of reduction ratio.

When the calcination is performed in a batchwise manner, the inert gas is supplied at a flow rate of not less than 50 N liters/hour/kg of the dried catalyst precursor, preferably in the range of from 50 to 5,000 N liters/hour/kg of the dried catalyst precursor, more preferably in the range of from 50 to 3,000 N liters/hour/kg of the dried catalyst precursor (wherein N liter means liter as measured under the normal temperature and pressure conditions, namely, at 0° C. under 1 atm.).

When the calcination is performed in a continuous manner, the inert gas is supplied at a flow rate of not less than 50 N liters/kg of the dried catalyst precursor, preferably in the range of from 50 to 5,000 N liters/kg of the dried catalyst precursor, more preferably in the range of from 50 to 3,000 N liters/kg of the dried catalyst precursor. In the case of the calcination performed in a continuous manner, there is no particular limitation with respect to the flow directions of the inert gas and the dried catalyst precursor, and the inert gas and the dried catalyst precursor may be supplied either in a counter flow mode or in a parallel flow mode. However, preferred is a counter flow mode, because gaseous substances are generated from the dried catalyst precursor, and a small amount of air comes into the calcination apparatus together with the dried catalyst precursor.

The reduction ratio of the obtained catalyst is generally influenced by the following factors: the amounts of organic substances contained in the dried catalyst precursor, such as an oxalic acid; the amount of ammonium radical derived from an ammonium salt used as a raw material; the rate of the heating temperature elevation at the time of starting of the calcination; the amount of inert gas, in the case where the calcination is conducted in an atmosphere of an inert gas; and the temperature and time of the calcination, in the case where the calcination is conducted in an atmosphere of air. For obtaining a catalyst which has a reduction ratio in the range of from 8 to 12%, it is important to calcine the dried catalyst precursor under calcination conditions wherein the heating temperature of the dried catalyst precursor is elevated from a temperature which is less than 400° C., to thereby decompose the oxalate radical, the ammonium radical and the like contained in the dried catalyst precursor, thereby substantially completing the generation of gas from the catalyst precursor, so that the catalyst precursor being calcined has a reduction ratio of from 8 to 12% when the heating temperature reaches 400° C.

On the other hand, the specific surface area of the obtained oxide catalyst is influenced by the heating temperature and time of the final calcination (final heating), and the amount of the silica carrier in the case of a catalyst comprising a silica carrier having supported thereon the oxide. However, the specific surface area of the obtained oxide catalyst is largely influenced, especially by the reduction ratio of the catalyst precursor at the time when the heating temperature reaches 400° C., and by the final heating temperature of the calcination. The final stage of the calcination is performed at a temperature in the range of from 550 to 700° C. for a time of from 0.5 to 20 hours. The higher the final heating temperature and the longer the final heating time, the smaller the specific surface area of the obtained catalyst. Also, the lower the reduction ratio of the catalyst precursor at the time when the heating temperature reaches 400° C., the smaller the specific surface area of the obtained catalyst; and, therefore, the higher the reduction ratio of the catalyst precursor at the time when the heating temperature reaches 400° C., the larger the specific surface area of the obtained catalyst. For obtaining a catalyst which has a specific surface area in the range of from 5 to 30 m$^2$/g, it is especially important to calcine the dried catalyst precursor under calcination conditions wherein the catalyst precursor being calcined has a reduction ratio of from 8 to 12% when the heating temperature reaches 400° C., and to perform the final stage of calcination at a heating temperature in the range of from 550 to 700° C.

The calcinacion can be performed in a single stage; however, for the purpose of efficiently producing a catalyst which has a reduction ratio in the range of from 8 to 12% and a specific surface area in the range of from 5 to 30 m$^2$/g, it is preferred that the calcination comprises a preliminary calcination and a final calcination, wherein the preliminary calcination is performed at a temperature in the range of from 250 to 400° C. and the final calcination is performed at a temperature in the range of from 550 to 700° C. The preliminary calcination and the final calcination may be performed either successively or completely separately. Further, each of the preliminary calcination and the final calcination may be performed in multiple stages.

For the measurement of the reduction ratio of the catalyst precursor being calcined, a specimen which is at the heating temperature may be quickly taken out of the calcination apparatus. However, since the heating temperature is high, it is possible that the catalyst precursor taken out is oxidized as it contacts air, thus causing the reduction ratio of the catalyst precursor to be changed. Therefore, for preventing a change in the reduction ratio of the catalyst precursor, it is desired that the catalyst precursor being calcined is allowed to cool in situ to room temperature before being taken out of the calcinating apparatus, and the catalyst precursor taken out in this manner is used as a representative specimen.

As specific examples of methods for causing the catalyst precursor being calcined to have a reduction ratio in the desired range when the heating temperature reaches 400° C., there can be mentioned the following methods: a method involving a control of the preliminary calcination temperature; a method involving an addition of an oxidant, such as oxygen, to an atmosphere in which the calcination is performed; a method involving an addition of a reductant to an atmosphere in which the calcination is performed; and a method of using the above-mentioned methods in combination. Hereinbelow, each method is described in detail.

The above-mentioned method involving a control of the preliminary calcination temperature is a method in which the temperature for the preliminary calcination is controlled so as to cause the catalyst precursor being calcined to have a reduction ratio in the desired range when the heating temperature reaches 400° C. Generally, the lower the preliminary calcination temperature, the lower the reduction ratio of the catalyst precursor being calcined; and, the higher the preliminary calcination temperature, the higher the reduction ratio of the catalyst precursor being calcined. This way, the reduction ratio of the catalyst precursor being calcined can be adjusted by controlling the preliminary calcination temperature.

When the calcination of the dried catalyst precursor is effected, the heating temperature of the dried catalyst precursor is continuously or intermittently elevated from a temperature which is less than 400° C., more preferably less than 250° C.

The preliminary calcination is preferably performed under a flow of an inert gas, at a heating temperature in the range of from 250 to 400° C., more advantageously in the range of from 300 to 400° C. It is preferred that the heating temperature is maintained at a constant level in the range of from 250 to 400° C.; however, the heating temperature may fluctuate, or may be slowly elevated or lowered within the range of from 250 to 400° C. It is preferred that the heating temperature is maintained for 30 minutes or more, more advantageously from 3 to 12 hours.

The elevation of the heating temperature before reaching the preliminary calcination temperature may be performed either at a constant rate so that the temperature elevation profile becomes a straight line, or at a non-constant rate so that the temperature elevation profile becomes a convex or concave curve.

With respect to the average temperature elevation rate during the elevation of the heating temperature before reaching the preliminary calcination temperature, there is no limitation; however, it is generally in the range of from about 0.1 to 15° C./min, preferably from 0.5 to 5° C./min, more preferably from 1 to 2° C./min.

The above-mentioned "method involving an addition of an oxidant, such as oxygen, to an atmosphere in which the calcination is performed" so as to cause the catalyst precursor being calcined to have a reduction ratio in the desired range when the heating temperature reaches 400° C., is a method which can be employed for the purpose of lowering the reduction ratio of the obtained catalyst. The term "calcination" means either or both of the preliminary calcination and the final calcination. The "oxidant" which is added to an atmosphere in which the calcination is performed means an oxidant which is contained in the inert gas supplied to the calcination apparatus. The amount of the oxidant added is adjusted by controlling the oxidant concentration of the inert gas supplied to the calcination apparatus. The reduction ratio can be controlled by adding an oxidant to the atmosphere in which the calcination is performed. When oxygen is used as the oxidant, it is preferred that air (or air-containing inert gas) is supplied to the calcination apparatus, thereby utilizing the oxygen in the air as the oxidant.

The above-mentioned "method involving an addition of a reductant to an atmosphere in which the calcination is performed" so as to cause the catalyst precursor being calcined to have a reduction ratio in the desired range when the heating temperature reaches 400° C., is a method which can be employed for the purpose of increasing the reduction ratio of the obtained catalyst. The term "calcination" means either or both of the preliminary calcination and the final calcination. The "reductant" which is added to an atmosphere in which the calcination is performed means a reductant which is contained in the inert gas supplied to the calcinating apparatus. The amount of the reductant added is adjusted by controlling the reductant concentration of the inert gas supplied to the calcinating apparatus. The reduction ratio can be controlled by adding a reductant to the atmosphere in which the calcination is performed. Generally, ammonia can be used as the reductant.

In the case where the catalyst precursor being calcined does not have a desired value of reduction ratio when the heating temperature reaches 400° C., a measure can be taken in which an oxidant or a reductant is added to the atmosphere in which the calcination is performed, thereby adjusting the reduction ratio, wherein the necessary amount of the oxidant or the reductant is calculated from the difference between the actual reduction ratio and the desired reduction ratio.

The final calcination is preferably performed under a flow of an inert gas, at a heating temperature in the range of from 550 to 700° C., more advantageously in the range of from 580 to 650° C. It is preferred that the heating temperature is maintained at a constant level in the range of from 550 to 700° C.; however, the heating temperature may fluctuate, or may be slowly elevated or lowered within the range of from 550 to 700° C. It is preferred that the final calcination is performed for a period of from 0.5 to 20 hours, more advantageously from 1 to 8 hours. During the final calcination, for the purpose of adjusting the reduction ratio of the catalyst precursor being calcined, if desired, an oxidant (e.g. oxygen) or a reductant (e.g. ammonia) may be added to the atmosphere in the final calcination under a flow of an inert gas.

The elevation of the heating temperature after the preliminary calcination and before reaching the final calcination temperature may be either at a constant rate so that the temperature elevation profile becomes a straight line, or at a non-constant rate so that the temperature elevation profile becomes a convex or concave curve.

With respect to the average temperature elevation rate during the elevation of the heating temperature after the preliminary calcination and before reaching the final calcination temperature, there is no limitation; however, it is generally in the range of from about 0.1 to 15° C./min, preferably from 0.5 to 10° C./min, more preferably from 1 to 5° C./min.

With respect to the average temperature lowering rate during the lowering of the heating temperature after completion of the final calcination, it is generally in the range of from about 0.01 to 100° C./min, preferably from 0.05 to 100° C./min, more preferably from 0.1 to 50° C./min, still more preferably from 0.5 to 10° C./min. It is also preferred that, during the temperature lowering, the heating temperature is temporarily maintained at a temperature lower than the final calcination temperature, wherein the temporarily maintained temperature is lower than the final calcination temperature by 5° C., more advantageously by 10° C., still more advantageously by 50° C. The time for which the temperature is maintained is preferably 0.5 hour or more, more preferably 1 hour or more, still more preferably 3 hours or more, still further more preferably 10 hours or more.

In the determination of the reduction ratio, the value of $(n_0-n)$ in formula (2) defining the reduction ratio of the oxide catalyst can be obtained by a method in which the specimen is subjected to a redox titration using $KMnO_4$. With respect to both of the catalyst precursor (before completion of the calcination) and the catalyst (after completion of the calcination), the value of $(n_0-n)$ in formula (2) can be obtained by a method in which the specimen is subjected to a redox titraion using $KMnO_4$. However, with respect to the conditions for the redox titration, there is a difference between the measuring operation in the case of the catalyst precursor (before completion of the calcination) and the measuring operation in the case of the catalyst (after completion of the calcination). For each of the catalyst precursor and the catalyst, an example of a method for measuring the value of $(n_0-n)$ in formula (2) is described below.

In the case of the catalyst precursor (before completion of the calcination), the measurement is performed as follows. About 200 mg of a specimen of the catalyst precursor is weighed and put in a beaker. An excess amount of an aqueous $KMnO_4$ solution having a predetermined concentration is added to the beaker. Then, 150 ml of purified water at 70° C. and 2 ml of a 1:1 sulfuric acid (i.e., an aqueous sulfuric acid solution obtained by mixing together a concentrated sulfuric acid and water in a volume ratio of 1/1) are added to the beaker, and the mouth of the beaker is covered with a watch glass, and the beaker is placed in a hot water bath at 70° C.±2° C., and the contents of the beaker are stirred for 1 hour, thereby oxidizing the specimen. Then, it is confirmed that the liquid in the beaker is purple since $KMnO_4$ was used in an excess amount and therefore an unreacted $KMnO_4$ is present in the liquid in the beaker. After the oxidization, the resultant reaction mixture in the beaker is subjected to filtration using a filter paper, and all filtrate is recovered. An aqueous sodium oxalate solution having a predetermined concentration is added to the recovered filtrate so that sodium oxalate $(Na_2C_2O_4)$ is used in an excess amount, relative to the $KMnO_4$ present in the filtrate. The resultant mixture is heated to 70° C. while stirring. It is confirmed that the mixture becomes colorless and transparent. Then, 2 ml of a 1:1 sulfuric acid is added to the mixture, and the resultant mixture is stirred and kept at 70° C.±2° C. With respect to the mixture, a titration using an aqueous $KMnO_4$ solution having a predetermined concentration is performed while stirring and keeping the mixture at 70° C.±2° C. The dripping of the aqueous $KMnO_4$ solution is ended when the mixture has a slight pink color which lasts for about 30 seconds. From all amount of $KMnO_4$ used and all amount of $Na_2C_2O_4$ used, the amount of $KMnO_4$ which was consumed for the oxidation of the specimen is determined. From this amount of $KMnO_4$, the value of $(n_0-n)$ in formula (2) is calculated. Based on the thus obtained value of $(n_0-n)$ in formula (2), the reduction ratio is obtained.

In the case of the catalyst (after completion of the calcination), the measurement is performed as follows. A specimen of the catalyst is ground in an agate mortar, and about 200 mg of the resultant ground specimen is weighed and put in a beaker. 150 ml of purified water at 95° C. and 4 ml of a 1:1 sulfuric acid (i.e., an aqueous sulfuric acid solution obtained by mixing together a concentrated sulfuric acid and water in a volume ratio of 1/1) are added to the beaker, and the resultant mixture is stirred and kept at 95° C.±2° C. With respect to the mixture, a titration using an aqueous $KMnO_4$ solution having a predetermined concentration is performed while stirring and keeping the mixture at 95° C.±2° C. In this instance, when the aqueous $KMnO_4$ solution is dripped into the mixture, the mixture temporarily has a purple color. The dripping of the aqueous $KMnO_4$ solution is slowly continued while confirming that the purple color does not last for 30 seconds or more. The amount of the mixture in the beaker gradually decreases in accordance with the evaporation of the water. Purified water at 95° C. is added to the mixture in the beaker so as to maintain the amount of the mixture at a constant level. The dripping of the aqueous $KMnO_4$ solution is finished when the mixture has a slight pink color which lasts for about 30 seconds. Thus, the amount of $KMnO_4$ which was consumed for the oxidation of the specimen is determined. From this amount of $KMnO_4$, the value of $(n_0-n)$ in formula (2) is calculated. Based on the thus obtained value of $(n_0-n)$ in formula (2), the reduction ratio is obtained.

In addition to the above-described method for determining the value of $(n_0-n)$ in formula (2), there can also be mentioned the below-described method, which can be used for both of the case of the catalyst precursor (before completion of the calcination) and the case of the catalyst (after completion of the calcination). The specimen (the catalyst precursor or the catalyst) is heated to a temperature which is higher than the highest temperature at which the specimen was heated during the calcination, thereby completely oxidizing the specimen with oxygen, wherein the heating is performed under conditions which can prevent volatilization and escaping of the component elements. By the heating, the weight of the specimen is increased due to the binding of oxygen. After the heating, the weight difference between the specimen after the heating and the specimen before the heating is measured. From the weight difference (the weight of the oxygen bound), the value of $(n_0-n)$ in formula (2) is calculated. Based on the thus obtained value of $(n_0-n)$ in formula (2), the reduction ratio is obtained.

The excellent catalyst of the present invention can be produced by the simple method as described herein above. The thus obtained catalyst of the present invention can be used for producing an unsaturated carboxylic acid, i.e., for producing acrylic acid or methacrylic acid by a process which comprises reacting propane or isobutane with molecular oxygen in the gaseous phase in the presence of the catalyst of the present invention. The catalyst of the present invention can also be used for producing an unsaturated nitrile, i.e., for producing acrylonitrile or methacrylonitrile by a process which comprises reacting propane or isobutane with ammonia and molecular oxygen in the gaseous phase in the presence of the catalyst of the present invention.

Propane, isobutane and ammonia used in the present invention need not be of a very high purity but may be of a commercial grade.

Examples of sources of molecular oxygen include air, pure oxygen and oxygen-rich air. Further, such a source of molecular oxygen may be diluted with helium, neon, argon, carbon dioxide, steam, nitrogen or the like.

In the ammoxidation reaction, the molar ratio of ammonia to propane or isobutane used for the ammoxidation is generally in the range of from 0.3 to 1.5, preferably from 0.8 to 1.2.

In each of the oxidation reaction and the ammoxidation reaction, the molar ratio of molecular oxygen to propane or isobutane used for the oxidation or ammoxidation is generally in the range of from 0.1 to 6, preferably from 0.1 to 4.

In each of the oxidation reaction and the ammoxidation reaction, the reaction pressure is generally in the range of from 0.5 to 5 atm, preferably from 1 to 3 atm.

In each of the oxidation reaction and the ammoxidation reaction, the reaction temperature is generally in the range of from 350 to 500° C., preferably from 380 to 470° C.

In each of the oxidation reaction and the ammoxidation reaction, the time of contact (contact time) between the gaseous feedstock mixture and the catalyst is generally in the range of from 0.1 to 10 (sec·g/cc), preferably from 0.5 to 5 (sec·g/cc).

In the present invention, the contact time is defined by the following formula:

contact time (sec·g/cc)=$(W/F) \times 273/(273+T) \times P$ wherein:
W represents the weight (g) of the catalyst,
F represents the flow rate (Ncc/sec) of the gaseous feedstock mixture in the standard state (0° C., 1 atm),
T represents the reaction temperature (0° C.), and
P represents the reaction pressure (atm).

Each of the oxidation reaction and the ammoxidation reaction can be conducted in a conventional reactor, such as a fixed bed reactor, a fluidized-bed reactor or a moving bed reactor. However, most preferred is a fluidized-bed reactor, because the use of a fluidized-bed reactor is advantageous in that the heat removal during the reaction can be easily performed, and therefore the temperature of the catalyst bed can be kept almost even, and that it is possible to take out the catalyst from the reactor and to feed an additional amount of catalyst to the reactor while operating the reactor.

For conducting the reaction on a commercial scale stably for a long time, it is preferred that a molybdenum compound is added to the reaction system. With respect to the molybdenum compound, there is no particular limitation, and any molybdenum compound can be used as long as the compound contains molybdenum element. However, from the viewpoint of easy handling and economy, it is preferred to use the same molybdenum compound as used in the production of the catalyst, for example, ammonium heptamolybdate. The catalyst of the present invention is advantageous in that, when a molybdenum compound is added to the catalytic oxidation or ammoxidation reaction system as conventionally practiced in the art for the purpose of maintaining a high yield by preventing a catalyst degradation caused by the volatilization or escaping of molybdenum from the catalyst, the amount of molybdenum compound added and the frequency of addition of molybdenum compound can be decreased, as compared to the case of the use of conventional catalysts, so that the reaction can be performed economically.

BEST MODE FOR CARRYING OUT THE INVENTION

Hereinbelow, the present invention will be described in more detail with reference to the following Examples and Comparative Examples, which should not be construed as limiting the scope of the present invention.

In the following Examples and Comparative Examples, the results of the ammoxidation were evaluated in terms of the conversion (%) of propane, the selectivity (%) for acrylonitrile, the yield (%) of acrylonitrile, and the catalyst activity, which are, respectively, defined as follows:

$$\text{Conversion}(\%) \text{ of propane} = \frac{\text{mole of propane reacted}}{\text{mole of propane fed}} \times 100$$

$$\frac{\text{Selectivity}(\%)}{\text{for acrylonitrile}} = \frac{\text{mole of acrylonitrile formed}}{\text{mole of propane reacted}} \times 100$$

$$\text{Yield}(\%) \text{ for acrylonitrile} = \frac{\text{mole of acrylonitrile formed}}{\text{mole of propane fed}}$$

Activity (hour$^{-1}$)=−3,600/(contact time)×ln((100−conversion of propane)/100)

(wherein ln is natural logarithm)

The Method for Measuring the Reduction Ratio:

In the case of the catalyst precursor (being calcined) at the time when the heating temperature reached 400° C., the measurement of the reduction ratio was performed as follows.

About 200 mg of a specimen of the catalyst precursor was weighed and put in a beaker. An excess amount of an aqueous KMnO$_4$ solution having a predetermined concentration was added to the beaker. Then, 150 ml of purified water at 70° C. and 2 ml of a 1:1 sulfuric acid (i.e., an aqueous sulfuric acid solution obtained by mixing together a concentrated sulfuric acid and water in a volume ratio of 1/1) were added to the beaker, and the mouth of the beaker was covered with a watch glass, and the beaker was placed in a hot water bath at 70° C.±2° C., and the contents of the beaker were stirred for 1 hour, thereby oxidizing the specimen. Then, it was confirmed that the liquid in the beaker was purple since $KMnO_4$ had been used in an excess amount and therefore an unreacted $KMnO_4$ was present in the liquid in the beaker. After the oxidization, the resultant reaction mixture in the beaker was subjected to filtration using a filter paper, and all filtrate was recovered. An aqueous sodium oxalate solution having a predetermined concentration was added to the recovered filtrate so that sodium oxalate ($Na_2C_2O_4$) was used in an excess amount, relative to the $KMnO_4$ present in the filtrate. The resultant mixture was heated to 70° C. while stirring. It was confirmed that the mixture became colorless and transparent. Then, 2 ml of a 1:1 sulfuric acid was added to the mixture, and the resultant mixture was stirred and kept at 70° C.±2° C. With respect to the mixture, a titration using an aqueous $KMnO_4$ solution having a predetermined concentration was performed while stirring and keeping the mixture at 70° C.±2° C. The dripping of the aqueous $KMnO_4$ solution was finished when the mixture had a slight pink color which lasted for about 30 seconds. From all amount of $KMnO_4$ used and all amount of $Na_2C_2O_4$ used, the amount of $KMnO_4$ which had been consumed for the oxidation of the specimen was determined. From this amount of $KMnO_4$, the value of $(n_0-n)$ in formula (2) was calculated. Based on the thus obtained value of $(n_0-n)$ in formula (2), the reduction ratio was obtained.

In the case of the catalyst (after completion of the calcination), the measurement of the reduction ratio was performed as follows.

A specimen of the catalyst was ground in an agate mortar, and about 200 mg of the resultant ground specimen was weighed and put in a beaker. 150 ml of purified water at 95° C. and 4 ml of a 1:1 sulfuric acid (i.e., an aqueous sulfuric acid solution obtained by mixing together a concentrated sulfuric acid and water in a volume ratio of 1/1) were added to the beaker, and the resultant mixture was stirred and kept at 95° C.±2° C. With respect to the mixture, a titration using an aqueous $KMnO_4$ solution having a predetermined concentration was performed while stirring and keeping the mixture at 95° C.±2° C. In this instance, when the aqueous $KMnO_4$ solution was dripped into the mixture, the mixture temporarily had a purple color. The dripping of the aqueous $KMnO_4$ solution was slowly continued while confirming that the purple color did not last for 30 seconds or more. The amount of the mixture in the beaker gradually decreased in accordance with the evaporation of the water. Purified water at 95° C. was added to the mixture in the beaker so as to maintain the amount of the mixture at a constant level. The dripping of the aqueous $KMnO_4$ solution was finished when the mixture had a slight pink color which lasted for about 30 seconds. Thus, the amount of $KMnO_4$ which had been consumed for the oxidation of the specimen was determined. From this amount of $KMnO_4$, the value of $(n_0-n)$ in formula (2) was calculated. Based on the thus obtained value of $(n_0-n)$ in formula (2), the reduction ratio was obtained.

The Method for Measuring the Specific Surface Area:

The specific surface area of the catalyst was measured by the BET method, using a surface area analyzer "GEMINI 2360" (manufactured by Micromeritics, U.S.A., imported and sold by Shimadzu Corporation, Japan).

<Preparation of a Niobium-containing Aqueous Solution>

In accordance with the method as disclosed in Unexamined Japanese Patent Application Laid-Open Specification No. Hei 11-253801, a niobium-containing aqueous solution was prepared as follows. To 8,450 g of water were added 1,290 g of niobic acid ($Nb_2O_5$ content: 80.2% by weight) and 4,905 g of oxalic acid dehydrate ($H_2C_2O_4.2H_2O$). The oxalic acid/niobium molar ratio in the resultant aqueous mixture was 5.0, and the niobium concentration of the resultant aqueous mixture was 0.532 mol/kg of the aqueous solution.

The obtained mixture was stirred at 95° C. for 1 hour, to thereby obtain a preliminary niobium-containing aqueous solution. The obtained preliminary niobium-containing aqueous solution was allowed to stand still while cooling with ice, to thereby precipitate solids. The precipitated solids in the solution were removed from the aqueous solution by suction filtration, to thereby obtain a homogenized niobium compound-containing aqueous solution.

The same procedure as described hereinabove was repeated several times, and the resultant niobium compound-containing aqueous solutions were mixed together, and the resultant mixture was designated the "niobium-containing aqueous solution". The oxalic acid/niobium molar ratio in the niobium-containing aqueous solution was 2.40, as determined by the following analysis method.

A 10 g sample solution was accurately taken from the niobium-containing aqueous solution and charged into a crucible. The sample solution was dried overnight at 95° C., followed by calcination at 600° C. for 1 hour, thereby obtaining 0.8639 g of $Nb_2O_5$. As a result, it was found that the niobium concentration of the niobium-containing aqueous solution was 0.65 mol/kg of the aqueous solution.

Next, the oxalic acid concentration of the niobium-containing aqueous solution was determined as follows. To a 300 ml glass beaker was added 3 g of sample solution accurately taken from the niobium-containing aqueous solution, followed by addition of 200 ml of water having a temperature of about 80° C. and 10 ml of aqueous sulfuric acid solution (volume ratio of concentrated sulfuric acid to water=1/1), to thereby obtain a test solution. The obtained test solution was subjected to titration using 1/4 N $KMnO_4$ solution, while stirring the test solution at 70° C. by using a hot stirrer. That is, the titration was conducted in accordance with the following reaction equation:

$$2KMnO_4+3H_2SO_4+5H_2C_2O_4 \rightarrow K_2SO_4+2MnSO_4+10CO_2+8H_2O.$$

An occurrence of a change in the color of the test solution in accordance with the progress of titration was examined. That is, the point at which the test solution was caused to assume a very light pink color due to the $KMnO_4$ and from which the test solution continued to have the very light pink color for 30 seconds or more, was defined as an end point of the titration. From the amount of 1/4 N $KMnO_4$ solution consumed, the oxalic acid concentration of the niobium-containing aqueous solution was calculated using the above reaction formula. As a result, it was found that the oxalic acid concentration of the niobium-containing aqueous solution was 1.56 mol/kg of the aqueous solution.

The thus obtained niobium-containing aqueous solution was used as the niobium-containing aqueous solution ($B_0$) in the following processes for producing catalysts.

EXAMPLE 1

An oxide catalyst represented by the formula: 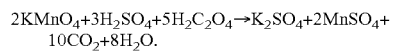 was prepared as follows.

(Preparation of an Aqueous Raw Material Mixture)

To 4,640 g of water were added 931.4 g of ammonium heptamolybdate [$(NH_4)_6Mo_7O_{24} \cdot 4H_2O$], 128.8 g of ammonium metavanadate ($NH_4VO_3$) and 153.1 g of diantimony trioxide ($Sb_2O_3$), and the resultant mixture was heated while stirring at 90° C. for 2.5 hours, thereby obtaining an aqueous mixture A-1.

On the other hand, to 725.3 g of the niobium-containing aqueous solution ($B_0$) was added 154.4 g of 30% by weight aqueous hydrogen peroxide ($H_2O_2$). To the resultant mixture was further added 30.6 g of diantimony trioxide ($Sb_2O_3$) slowly while keeping the temperature at about 20° C., followed by stirring, to thereby obtain an aqueous liquid B-1.

Subsequently, the above-obtained aqueous mixture A-1 was cooled to 70° C., followed by addition of 1,960 g of a silica sol having an $SiO_2$ content of 30.6% by weight. Then, to the resultant mixture was further added 178.2 g of 30% by weight aqueous hydrogen peroxide ($H_2O_2$), and the resultant mixture was stirred at 50° C. for 1 hour. To the resultant mixture was further added the aqueous liquid B-1 to obtain a mixture. To the obtained mixture was further added a liquid obtained by dispersing 300 g of a fumed silica having an average primary particle diameter of about 12 nm into 4,500 g of water, to thereby obtain an aqueous raw material mixture.

(Preparation of a Dried Catalyst Precursor)

The thus obtained aqueous raw material mixture was subjected to spray drying using a centrifugation type spray-drying apparatus, to thereby obtain a dried, microspherical particulate catalyst precursor. The inlet and outlet temperatures of the dryer section of the apparatus were 210° C. and 120° C., respectively.

(Calcination)

480 g of the obtained dried catalyst precursor was charged into a SUS calcination tube (inner diameter: 3 inch), and then calcination was performed under a stream of nitrogen gas at a flow rate of 1.5 N liters/min while rotating the calcination tube, under conditions wherein the heating temperature was elevated to 345° C. over about 4 hours and then maintained at 345° C. for 4 hours, and then, the heating temperature was elevated to 640° C. over 2 hours and then maintained at 640° C. for 2 hours, to thereby obtain an oxide catalyst. During the calcination, when the heating temperature reached 400° C., a part (specimen) of the catalyst precursor being calcined was taken out of the calcination tube so as not to cause a reduction of the specimen, and the reduction ratio of the specimen of catalyst precursor was measured. It was found that the catalyst precursor had a reduction ratio of 10.3%.

The measurement of the reduction ratio was also performed with respect to the catalyst (after completion of the calcination). It was found that the obtained catalyst had a reduction ratio of 10.3%.

The specific surface area of the obtained catalyst was measured by the BET method using the above-mentioned surface area analyzer "GEMINI 2360", and it was found that the catalyst had a surface area of 16 $m^2/g$.

EXAMPLE 2

An oxide catalyst represented by the formula: $Mo_1V_{0.21}Nb_{0.09}Sb_{0.24}O_n/SiO_2$(45% by weight) was prepared as follows.

(Preparation of an Aqueous Raw Material Mixture)

To 4,640 g of water were added 931.4 g of ammonium heptamolybdate [$(NH_4)_6Mo_7O_{24} \cdot 4H_2O$], 128.8 g of ammonium metavanadate ($NH_4VO_3$) and 183.8 g of diantimony trioxide ($Sb_2O_3$), and the resultant mixture was heated while stirring at 90° C. for 2.5 hours, thereby obtaining an aqueous mixture A-2.

On the other hand, to 725.3 g of the niobium-containing aqueous solution ($B_0$) was added 106.9 g of 30% by weight aqueous hydrogen peroxide ($H_2O_2$), followed by stirring, to thereby obtain an aqueous liquid B-2.

Subsequently, the above-obtained aqueous mixture A-2 was cooled to 70° C., followed by addition of 1,960 g of a silica sol having an $SiO_2$ content of 30.6% by weight. Then, to the resultant mixture was further added 213.8 g of 30% by weight aqueous hydrogen peroxide ($H_2O_2$), and the resultant mixture was stirred at 50° C. for 1 hour. To the resultant mixture was further added the aqueous liquid B-2 to obtain a mixture. To the obtained mixture was further added a liquid obtained by dispersing 300 g of a fumed silica having an average primary particle diameter of about 12 nm into 4,500 g of water, to thereby obtain an aqueous raw material mixture.

(Preparation of a Dried Catalyst Precursor)

The thus obtained aqueous raw material mixture was subjected to spray drying using a centrifugation type spray-drying apparatus, to thereby obtain a dried, microspherical particulate catalyst precursor. The inlet and outlet temperatures of the dryer section of the apparatus were 210° C. and 120° C., respectively.

The above-described procedure for producing an aqueous raw material mixture and producing a dried catalyst precursor was repeated five times, and the resultant dried catalyst precursors were mixed together. The thus obtained dried catalyst precursor was then subjected to calcination as described below.

(Calcination)

The obtained dried catalyst precursor was fed at a feeding rate of 80 g/hour into a SUS continuous calcination apparatus having a calcination tube (inner diameter: 3 inch; length: 89 cm), and then calcination was performed under a stream of nitrogen gas fed in a counter flow (i.e., in a flow direction opposing the feeding direction of the dried catalyst precursor) at a flow rate of 1.5 N liters/min while rotating the calcination tube, under conditions wherein the heating temperature was elevated to 345° C. over about 4 hours and then maintained at 345° C. for 4 hours. The resultant preliminarily calcined catalyst precursor was collected at the outlet of the calcination tube. A part (specimen) of the preliminarily calcined catalyst precursor was taken and heated in a nitrogen atmosphere to 400° C., and then the reduction ratio of the specimen of preliminarily calcined catalyst precursor was measured. It was found that the preliminarily calcined catalyst precursor had a reduction ratio of 10.4%.

The obtained preliminarily calcined catalyst precursor was fed at a feeding rate of 130 g/hour into a SUS continuous calcination apparatus having a calcination tube (inner diameter: 3 inch; length: 89 cm), and then calcination was performed under a stream of nitrogen gas at a flow rate of 1.5 N liters/min while rotating the calcination tube, under conditions wherein the heating temperature was elevated to 640° C. over about 4 hours and then maintained at 640° C. for 2 hours, to thereby obtain a catalyst. The obtained catalyst (after completion of the final calcination) was collected at the outlet of the calcination tube. The reduction ratio and specific surface area of the catalyst were measured. It was found that the catalyst had a reduction ratio of 10.4% and a specific surface area of 17 m$^2$/g.

EXAMPLE 3

Using the dried catalyst precursor obtained in Example 2, the calcination was performed in substantially the same manner as in Example 1, except that the heating temperatures for the preliminary calcination and the final calcination were 350° C. and 620° C., respectively. During the calcination, when the heating temperature reached 400° C., a part (specimen) of the catalyst precursor being calcined was taken out of the calcination tube so as not to cause a reduction of the specimen, and the reduction ratio of the specimen of catalyst precursor was measured. It was found that the catalyst precursor had a reduction ratio of 10.8%. The reduction ratio and specific surface area of the catalyst (after completion of the calcination) were measured. It was found that the catalyst had a reduction ratio of 10.8% and a specific surface area of 19 m$^2$/g.

COMPARATIVE EXAMPLE 1

An oxide catalyst represented by the formula: $Mo_1V_{0.21}Nb_{0.09}Sb_{0.24}O_n/SiO_2$(45% by weight) was prepared as follows.

(Preparation of an Aqueous Raw Material Mixture)

To 4,640 g of water were added 931.4 g of ammonium heptamolybdate [$(NH_4)_6Mo_7O_{24}.4H_2O$], 128.8 g of ammonium metavanadate ($NH_4VO_3$) and 183.8 g of diantimony trioxide ($Sb_2O_3$), and the resultant mixture was heated while stirring at 90° C. for 2.5 hours, thereby obtaining an aqueous mixture A-3.

On the other hand, 725.3 g of the niobium-containing aqueous solution (Bo) was taken and designated an aqueous liquid B-3.

Subsequently, the above-obtained aqueous mixture A-3 was cooled to 70° C., followed by addition of 1,960 g of a silica sol having an SiO$_2$ content of 30.6% by weight. Then, to the resultant mixture was further added the aqueous liquid B-3 to obtain a mixture. To the obtained mixture was further added a liquid obtained by dispersing 300 g of a fumed silica having an average primary particle diameter of about 12 nm into 4,500 g of water, to thereby obtain an aqueous raw material mixture.

(Preparation of a Dried Catalyst Precursor)

The thus obtained aqueous raw material mixture was subjected to spray drying using a centrifugation type spray-drying apparatus, to thereby obtain a dried, microspherical particulate catalyst precursor. The inlet and outlet temperatures of the dryer section of the apparatus were 210° C. and 120° C., respectively.

(Calcination)

480 g of the obtained dried catalyst precursor was charged into a SUS calcination tube (inner diameter: 3 inch), and then calcination was performed under a stream of nitrogen gas at a flow rate of 1.5 N liters/min while rotating the calcination tube, under conditions wherein the heating temperature was elevated to 345° C. over about 4 hours and then maintained at 345° C. for 4 hours, and then, the heating temperature was elevated to 660° C. over 2 hours and then maintained at 660° C. for 2 hours, to thereby obtain an oxide catalyst. During the calcination, when the heating temperature reached 400° C., a part (specimen) of the catalyst precursor being calcined was taken out of the calcination tube so as not to cause a reduction of the specimen, and the reduction ratio of the specimen of catalyst precursor was measured. It was found that the catalyst precursor had a reduction ratio of 15.4%. The reduction ratio and specific surface area of the catalyst (after completion of the calcination) were measured. It was found that the catalyst had a reduction ratio of 15.5% and a specific surface area of 25 m$^2$/g.

COMPARATIVE EXAMPLE 2

An oxide catalyst represented by the formula: $Mo_1V_{0.21}Nb_{0.09}Sb_{0.24}O_n/SiO_2$(45% by weight) was prepared as follows.

(Preparation of an Aqueous Raw Material Mixture and a Dried Catalyst Precursor)

A dried catalyst precursor was prepared in substantially the same manner as in Comparative Example 1.

(Calcination)

480 g of the obtained dried catalyst precursor was charged into a SUS calcination tube (inner diameter: 3 inch), and then calcination was performed under a stream of air at a flow rate of 1.5 N liters/min while rotating the calcination tube, under conditions wherein the heating temperature was elevated to 400° C. over about 4 hours and then maintained at 400° C. for 4 hours, and then, the heating temperature was elevated to 640° C. over 2 hours and then maintained at 640° C. for 2 hours, to thereby obtain an oxide catalyst. During the calcination, when the heating temperature reached 400° C., a part (specimen) of the catalyst precursor being calcined was taken out of the calcination tube so as not to cause a reduction of the specimen, and the reduction ratio of the specimen of catalyst precursor was measured. It was found that the catalyst precursor had a reduction ratio of 1.1%. The reduction ratio and specific surface area of the catalyst (after completion of the calcination) were measured. It was found that the catalyst had a reduction ratio of 1.0% and a specific surface area of 11 m$^2$/g.

COMPARATIVE EXAMPLE 3

Using the dried catalyst precursor obtained in Example 2, the calcination was performed in substantially the same manner as in Example 1, except that the heating temperatures for the preliminary calcination and the final calcination were 460° C. and 640° C., respectively. During the calcination, when the heating temperature reached 400° C., a part (specimen) of the catalyst precursor being calcined was taken out of the calcination tube so as not to cause a reduction of the specimen, and the reduction ratio of the specimen of catalyst precursor was measured. It was found that the catalyst precursor had a reduction ratio of 13.2%. The reduction ratio and specific surface area of the catalyst (after completion of the calcination) were measured. It was found that the catalyst had a reduction ratio of 13.2% and a specific surface area of 21 m$^2$/g.

COMPARATIVE EXAMPLE 4

Using the dried catalyst precursor obtained in Example 2, the calcination was performed in substantially the same manner as in Example 1, except that the heating temperatures for the preliminary calcination and the final calcination were 350° C. and 500° C., respectively. During the calcination, when the heating temperature reached 400° C., a part (specimen) of the catalyst precursor being calcined was taken out of the calcination tube so as not to cause a reduction of the specimen, and the reduction ratio of the specimen of catalyst precursor was measured. It was found that the catalyst precursor had a reduction ratio of 10.8%. The reduction ratio and specific surface area of the catalyst (after completion of the calcination) were measured. It was found that the catalyst had a reduction ratio of 10.8% and a specific surface area of 45 $m^2/g$.

COMPARATIVE EXAMPLE 5

Using the dried catalyst precursor obtained in Example 2, the calcination was performed in substantially the same manner as in Example 1, except that the heating temperatures for the preliminary calcination and the final calcination were 350° C. and 800° C., respectively. During the calcination, when the heating temperature reached 400° C., a part (specimen) of the catalyst precursor being calcined was taken out of the calcination tube so as not to cause a reduction of the specimen, and the reduction ratio of the specimen of catalyst precursor was measured. It was found that the catalyst precursor had a reduction ratio of 10.7%. The reduction ratio and specific surface area of the catalyst (after completion of the calcination) were measured. It was found that the catalyst had a reduction ratio of 10.8% and a specific surface area of 4 $m^2/g$.

EXAMPLE 4

Using the dried catalyst precursor obtained in Example 2, the calcination was performed in substantially the same manner as in Example 1, except that the calcination was performed under a stream of nitrogen gas containing 400 ppm oxygen, and that the heating temperatures for the preliminary calcination and the final calcination were 460° C. and 640° C., respectively. During the calcination, when the heating temperature reached 400° C., a part (specimen) of the catalyst precursor being calcined was taken out of the calcination tube so as not to cause a reduction of the specimen, and the reduction ratio of the specimen of catalyst precursor was measured. It was found that the catalyst precursor had a reduction ratio of 11.0%. The reduction ratio and specific surface area of the catalyst (after completion of the calcination) were measured. It was found that the catalyst had a reduction ratio of 11.1% and a specific surface area of 18 $m^2/g$.

EXAMPLE 5

(Evaluation of the Catalyst Activity)

2.0 g of the oxide catalyst obtained in Example 1 was charged into a fixed-bed type reaction tube having an inner diameter of 10 mm. A gaseous feedstock mixture having a molar ratio of propane:ammonia:oxygen:helium of 1:1.2:2.8:11 was fed into the reaction tube. The reaction temperature was 440° C., and the reaction pressure was the normal pressure, namely, under 1 atm. The contact time between the oxide catalyst and the gaseous mixture of the feedstocks was 2.8 (sec·g/cc). The results are shown in Table 1.

(Evaluation of the Yield of Acrylonitrile)

45 g of the oxide catalyst obtained in Example 1 was charged into a Vycor glass fluidized-bed type reaction tube having an inner diameter of 25 mm. A gaseous feedstock mixture having a molar ratio of propane:ammonia:oxygen:helium of 1:1:3.2:12 was fed into the reaction tube. The reaction temperature was 440° C., the reaction pressure was the normal pressure, namely, under 1 atm, and the contact time was 3.2 (sec·g/cc).

0.1 g of ammonium heptamolybdate was added to the reaction system, 1,600 hours after the start of the reaction. The results are shown in Table 2.

EXAMPLE 6

(Evaluation of the Catalyst Activity)

Using the oxide catalyst obtained in Example 2, the ammoxidation of propane was performed for evaluating the catalyst activity, in substantially the same manner as in Example 5. The results are shown in Table 1.

(Evaluation of the Yield of Acrylonitrile)

Using the oxide catalyst obtained in Example 2, the ammoxidation of propane was performed for evaluating the yield of acrylonitrile, in substantially the same manner as in Example 5. The results are shown in Table 2.

EXAMPLE 7

(Evaluation of the Catalyst Activity)

Using the oxide catalyst obtained in Example 3, the ammoxidation of propane was performed for evaluating the catalyst activity, in substantially the same manner as in Example 5. The results are shown in Table 1.

(Evaluation of the Yield of Acrylonitrile)

Using the oxide catalyst obtained in Example 3, the ammoxidation of propane was performed for evaluating the yield of acrylonitrile, in substantially the same manner as in Example 5. The results are shown in Table 2.

COMPARATIVE EXAMPLE 6

(Evaluation of the Catalyst Activity)

Using the oxide catalyst obtained in Comparative Example 1, the ammoxidation of propane was performed for evaluating the catalyst activity, in substantially the same manner as in Example 5. The results are shown in Table 1.

(Evaluation of the Yield of Acrylonitrile)

Using the oxide catalyst obtained in Comparative Example 1, the ammoxidation of propane was performed for evaluating the yield of acrylonitrile, in substantially the same manner as in Example 5, except that the reaction was terminated 24 hours after the start of the reaction, because of too low an yield obtained. The results are shown in Table 2.

COMPARATIVE EXAMPLE 7

(Evaluation of the Catalyst Activity)

Using the oxide catalyst obtained in Comparative Example 2, the ammoxidation of propane was performed for evaluating the catalyst activity, in substantially the same manner as in Example 5. The results are shown in Table 1.

(Evaluation of the Yield of Acrylonitrile)

Using the oxide catalyst obtained in Comparative Example 2, the ammoxidation of propane was performed for evaluating the yield of acrylonitrile, in substantially the same manner as in Example 5, except that the reaction was terminated 24 hours after the start of the reaction, because of too low an yield obtained. The results are shown in Table 2.

COMPARATIVE EXAMPLE 8

(Evaluation of the Catalyst Activity)

Using the oxide catalyst obtained in Comparative Example 3, the ammoxidation of propane was performed for evaluating the catalyst activity, in substantially the same manner as in Example 5. The results are shown in Table 1.

(Evaluation of the Yield of Acrylonitrile)

Using the oxide catalyst obtained in Comparative Example 3, the ammoxidation of propane was performed for evaluating the yield of acrylonitrile, in substantially the same manner as in Example 5, except that 100 hours and 200 hours after the start of the reaction, ammonium heptamolybdate was added to the reaction system, each time in an amount of 0.1 g. The results are shown in Table 2.

COMPARATIVE EXAMPLE 9

(Evaluation of the Catalyst Activity)

Using the oxide catalyst obtained in Comparative Example 4, the ammoxidation of propane was performed for evaluating the catalyst activity, in substantially the same manner as in Example 5. The results are shown in Table 1.

(Evaluation of the Yield of Acrylonitrile)

Using the oxide catalyst obtained in Comparative Example 4, the ammoxidation of propane was performed for evaluating the yield of acrylonitrile, in substantially the same manner as in Example 5, except that the reaction was terminated 24 hours after the start of the reaction, because of too low an yield obtained. The results are shown in Table 2.

COMPARATIVE EXAMPLE 10

(Evaluation of the Catalyst Activity)

Using the oxide catalyst obtained in Comparative Example 5, the ammoxidation of propane was performed for evaluating the catalyst activity, in substantially the same manner as in Example 5. The results are shown in Table 1.

(Evaluation of the Yield of Acrylonitrile)

Using the oxide catalyst obtained in Comparative Example 5, the ammoxidation of propane was performed for evaluating the yield of acrylonitrile, in substantially the same manner as in Example 5, except that the reaction was terminated 24 hours after the start of the reaction, because of too low an yield obtained. The results are shown in Table 2.

EXAMPLE 8

(Evaluation of the Catalyst Activity)

Using the oxide catalyst obtained in Example 4, the ammoxidation of propane was performed for evaluating the catalyst activity, in substantially the same manner as in Example 5. The results are shown in Table 1.

(Evaluation of the Yield of Acrylonitrile)

Using the oxide catalyst obtained in Example 4, the ammoxidation of propane was performed for evaluating the yield of acrylonitrile, in substantially the same manner as in Example 5. The results are shown in Table 2.

TABLE 1

| | Activity ($10^3$ hour$^{-1}$) |
|---|---|
| Ex. 5 | 2.8 |
| Ex. 6 | 2.7 |
| Ex. 7 | 3.0 |
| Compara. Ex. 6 | 0.8 |
| Compara. Ex. 7 | 0.1 |
| Compara. Ex. 8 | 1.5 |
| Compara. Ex. 9 | 1.1 |
| Compara. Ex. 10 | 0.4 |
| Ex. 8 | 2.6 |

TABLE 2

| | Reaction time (hours) | Conversion of propane (%) | Selectivity for acrylonitrile (%) | Yield of acrylonitrile (%) |
|---|---|---|---|---|
| Ex. 5 | 24 | 90.6 | 59.1 | 53.5 |
| | 240 | 91.0 | 58.9 | 53.6 |
| | 1300 | 91.1 | 58.7 | 53.5 |
| | 1500 | 90.9 | 58.4 | 53.1 |
| | 1700 | 91.0 | 59.0 | 53.7 |
| | 2200 | 90.8 | 58.9 | 53.5 |
| Ex. 6 | 24 | 90.5 | 58.8 | 53.2 |
| | 2200 | 90.7 | 58.5 | 53.1 |
| Ex. 7 | 24 | 91.8 | 58.2 | 53.4 |
| | 2200 | 91.5 | 58.3 | 53.3 |
| Compara. Ex. 6 | 24 | 47.3 | 22.2 | 10.5 |
| Compara. Ex. 7 | 24 | 7.7 | 5.2 | 0.4 |
| Compara. Ex. 8 | 24 | 71.9 | 47.6 | 34.2 |
| | 240 | 68.8 | 47.2 | 32.5 |
| Compara. Ex. 9 | 24 | 60.7 | 24.5 | 14.9 |
| Compara. Ex. 10 | 24 | 27.4 | 29.9 | 8.2 |
| Ex. 8 | 24 | 88.9 | 58.9 | 52.4 |
| | 2200 | 88.5 | 59.1 | 52.3 |

INDUSTRIAL APPLICABILITY

The catalyst of the present invention is advantageous not only in that the selectivity for and yield of the desired product in the oxidation or ammoxidation are high, but also in that the catalyst exhibits only a small lowering of the yield of the desired product even in a long reaction time. Therefore, when the catalyst of the present invention is used for performing a catalytic oxidation or ammoxidation of propane or isobutane in the gaseous phase, an unsaturated carboxylic acid or an unsaturated nitrile (namely, (meth)acrylic acid or (meth)acrylonitrile) can be produced stably in high yield for a long period of time. Further, since the catalyst of the present invention exhibits only a small lowering of the yield with the passage of reaction time, the catalyst of the present invention is also advantageous in that, when a molybdenum compound is added to the catalytic oxidation or ammoxidation reaction system as conventionally practiced in the art for the purpose of maintaining a high yield by preventing a catalyst degradation caused by the volatilization or escaping of molybdenum from the catalyst, the amount of molybdenum compound added and the frequency of addition of molybdenum compound can be decreased, as compared to the case of the use of conventional catalysts, so that the reaction can be performed economically. In addition, the catalyst of the present invention is advantageous in that a moderate catalyst activity can be exhibited, and hence there can be prevented problems that too large an amount of catalyst is required for the reaction, thus causing too heavy a load on the reactor and that the heat of reaction generated becomes too large, rendering it impossible to effect a satisfactory heat removal from the reaction system.

The invention claimed is:

1. A catalyst for use in catalytic oxidation or ammoxidation of propane or isobutane in the gaseous phase, which comprises an oxide and a silica carrier having supported thereon said oxide, wherein said silica carrier is present in an amount of from 20 to 60% by weight in terms of $SiO_2$, based on the total weight of said oxide and said silica carrier, said oxide being represented by the following formula (1):

$$Mo_1V_aNb_bSb_cO_n \qquad (1)$$

wherein:

a, b, c and n are, respectively, the atomic ratios of vanadium (V), niobium (Nb), antimony (Sb) and oxygen (O), relative to molybdenum (Mo), wherein:

$0.1 \leq a \leq 1$, $0.01 \leq b \leq 1$, $0.01 \leq c \leq 1$, and n is the number of oxygen atoms required to satisfy the valence requirements of the other component elements present, said catalyst having a reduction ratio of from 8 to 12% and a specific surface area of from 7 to 30 $m^2/g$, said reduction ratio being represented by the following formula (2):

$$\text{reduction ratio (\%)} = ((n_0 - n)/n_0) \times 100 \qquad (2)$$

wherein:

n is as defined for formula (1), and $n_0$ is the number of oxygen atoms required when the other component elements in said oxide of formula (1) respectively exhibit the maximum oxidation numbers of the other component elements.

2. The catalyst according to claim 1, wherein a, b and c in formula (1) are as follows:

$0.1 \leq a \leq 0.3$, $0.05 \leq b \leq 0.2$, $0.1 \leq c \leq 0.3$.

3. The catalyst according to claim 1 or 2, wherein $n_0$ in formula (2) is from 4 to 5.

4. A process for producing the catalyst of claim 1, which comprises the steps of:

providing an aqueous raw material mixture containing compounds of molybdenum, vanadium, niobium and antimony and a source of silica, drying said aqueous raw material mixture to thereby obtain a dried catalyst precursor, and calcining said dried catalyst precursor under calcination conditions wherein the heating temperature of said dried catalyst precursor is continuously or intermittently elevated from a temperature which is less than 400° C. to a temperature which is in the range of from 550 to 700° C., wherein said calcination conditions are adjusted so that said catalyst precursor being calcined has a reduction ratio of from 8 to 12% when the heating temperature reaches 400° C., wherein said reduction ratio is as defined in claim 1, thereby obtaining a catalyst having a reduction ratio of from 8 to 12% and a specific surface area of from 7 to 30 $m^2/g$.

5. The process according to claim 4, wherein said aqueous raw material mixture is obtained by mixing an aqueous mixture (A) containing compounds of molybdenum, vanadium and antimony with an aqueous liquid (B) containing a niobium compound.

6. The process according to claim 5, wherein said aqueous mixture (A) is obtained by heating, at 50° C. or more, compounds of molybdenum, vanadium and antimony in an aqueous solvent.

7. The process according to claim 6, wherein, after said heating, hydrogen peroxide is added to said aqueous mixture (A).

8. The process according to claim 7, wherein the amount of said hydrogen peroxide is such that the molar ratio ($H_2O_2$/Sb molar ratio) of said hydrogen peroxide to said antimony compound in terms of antimony is in the range of from 0.01 to 20.

9. The process according to claim 5, wherein said aqueous liquid (B) contains a dicarboxylic acid in addition to said niobium compound, wherein the molar ratio (dicarboxylic acid/Nb molar ratio) of said dicarboxylic acid to said niobium compound in terms of niobium is in the range of from 1 to 4.

10. The process according to claim 5 or 9, wherein at least a part of said aqueous liquid (B) containing a niobium compound is used in the form of a mixture thereof with hydrogen peroxide.

11. The process according to claim 10, wherein the amount of said hydrogen peroxide is such that the molar ratio ($H_2O_2$/Nb molar ratio) of said hydrogen peroxide to said niobium compound in terms of niobium is in the range of from 0.5 to 20.

12. The process according to claim 5 or 9, wherein at least a part of said aqueous liquid (B) containing a niobium compound is used in the form of a mixture thereof with hydrogen peroxide and an antimony compound.

13. The process according to claim 12, wherein:

the amount of said hydrogen peroxide is such that the molar ratio ($H_2O_2$/Nb molar ratio) of said hydrogen peroxide to said niobium compound in terms of niobium is in the range of from 0.5 to 20, and the amount of said antimony compound mixed with the at least a part of said aqueous liquid (B) and said hydrogen peroxide is such that the molar ratio (Sb/Nb molar ratio) of said antimony compound in terms of antimony to said niobium compound in terms of niobium is not more than 5.

14. The process according to claim 4, wherein at least a part of said calcination is performed in an atmosphere of an inert gas, wherein:

when said calcination is performed in a batchwise manner, said inert gas is supplied at a flow rate of not less than 50 N liters/hour/kg of said dried catalyst precursor, and when said calcination is performed in a continuous manner, said inert gas is supplied at a flow rate of not less than 50 N liters/kg of said dried catalyst precursor.

15. The process according to claim 4 or 14, wherein said calcination comprises a preliminary calcination and a final calcination, wherein said preliminary calcination is performed at a temperature in the range of from 250 to 400° C. and said final calcination is performed at a temperature in the range of from 550 to 700° C.

16. The process according to claim 4 or 14, wherein, during said calcination, an oxidant or a reductant is added to an atmosphere in which said calcination is performed, so as to cause said catalyst precursor being calcined to have a reduction ratio of from 8 to 12% when the heating temperature reaches 400° C.

17. The process according to claim 16, wherein said oxidant is oxygen gas.

18. The process according to claim 16, wherein said reductant is ammonia.

19. A process for producing acrylic acid or methacrylic acid, which comprises reacting propane or isobutane with molecular oxygen in the gaseous phase in the presence of the catalyst of claim 1.

20. A process for producing acrylonitrile or methacrylonitrile, which comprises reacting propane or isobutane with ammonia and molecular oxygen in the gaseous phase in the presence of the catalyst of claim 1.

* * * * *